United States Patent [19]
Hauer et al.

[11] Patent Number: 6,007,840
[45] Date of Patent: *Dec. 28, 1999

[54] PHARMACEUTICAL COMPOSITIONS COMPRISING CYCLOSPORINS

[75] Inventors: Birgit Hauer, Lahr; Armin Meinzer, Freiburg/Munzingen; Ulrich Posanski, Freiburg, all of Germany; Friedrich Richter, Schönbühl-Urtenen, Switzerland

[73] Assignee: Novartis AG, Basel, Switzerland

[*] Notice: This patent is subject to a terminal disclaimer.

[21] Appl. No.: 09/184,547

[22] Filed: Nov. 2, 1998

Related U.S. Application Data

[62] Division of application No. 08/811,749, Mar. 6, 1997, Pat. No. 5,866,159, which is a division of application No. 08/430,770, Apr. 27, 1995, Pat. No. 5,741,512, which is a continuation of application No. 08/259,951, Jun. 15, 1994, abandoned, which is a division of application No. 07/990,734, Dec. 15, 1992, Pat. No. 5,342,625, which is a continuation of application No. 07/680,211, Apr. 4, 1991, abandoned, which is a continuation of application No. 07/406,656, Sep. 13, 1989, abandoned.

[30] Foreign Application Priority Data

| Sep. 16, 1988 | [GB] | United Kingdom | 8821754 |
| Feb. 9, 1989 | [GB] | United Kingdom | 8902900 |
| Feb. 9, 1989 | [GB] | United Kingdom | 8902903 |

[51] Int. Cl.⁶ ............. A61K 9/127; A61K 9/107; A61K 38/13
[52] U.S. Cl. ............. 424/450; 424/455; 514/11; 514/937; 514/938
[58] Field of Search ............. 424/400, 455, 424/450; 514/11, 937, 938–945

[56] References Cited

U.S. PATENT DOCUMENTS

| 3,288,824 | 11/1966 | Mahler et al. | 260/410.6 |
| 3,813,345 | 5/1974 | Urton | 252/312 |
| 3,954,967 | 5/1976 | Urton | 424/78 |
| 4,073,943 | 2/1978 | Wretlind et al. | 424/358 |
| 4,146,499 | 3/1979 | Rosano | 252/186 |
| 4,156,719 | 5/1979 | Sezaki et al. | 424/177 |
| 4,388,307 | 6/1983 | Cavanak | 424/177 |
| 4,567,161 | 1/1986 | Posanski et al. | 424/199 |
| 4,695,450 | 9/1987 | Bauer et al. | 424/168 |
| 4,719,239 | 1/1988 | Muller et al. | 514/785 |
| 4,794,000 | 12/1988 | Ecanow | 424/457 |
| 4,797,272 | 1/1989 | Linn et al. | 424/59 |
| 4,797,273 | 1/1989 | Linn et al. | 424/59 |
| 4,798,823 | 1/1989 | Witzel | 514/11 |

(List continued on next page.)

FOREIGN PATENT DOCUMENTS

| 8770043 | 2/1987 | Australia . |
| 895724 | 7/1983 | Belgium . |
| 1209361 | 8/1986 | Canada . |

(List continued on next page.)

OTHER PUBLICATIONS

95:225610K, Anon. (1981).
Anon., Research Disclosure 21143 (Nov. 1981).
Beyer, et al., Pamazie in unserer Zeit, vol. 12(2):55–60 (1983).
Bhargava, et al., Pharmaceutical Technology, Mar., 1987.

(List continued on next page.)

Primary Examiner—Gollamudi S. Kishore
Attorney, Agent, or Firm—Stephen G. Kalinchak

[57] ABSTRACT

Pharmaceutical compositions comprising a cyclosporin, e.g. Ciclosporin or [Nva]²-Ciclosporin, in "microemulsion preconcentrate" and microemulsion form. The compositions typically comprise (1.1) a $C_{1-5}$ alkyl or tetrahydrofurfuryl di- or partial-ether of a low molecular weight mono- or polyoxy-alkane diol, e.g. Transcutol or Glycofurol, as hydrophilic component. Compositions are also provided comprising a cyclosporin and (1.1) and, suitably, also a saccharide monoester, e.g. raffinose or saccharose monolaurate. Dosage forms include topical formulations and, in particular, oral dosage forms.

96 Claims, 4 Drawing Sheets

U.S. PATENT DOCUMENTS

| | | | |
|---|---|---|---|
| 4,835,002 | 5/1989 | Wolf et al. | 426/590 |
| 4,888,239 | 12/1989 | Brox | 428/402.2 |
| 4,914,188 | 4/1990 | Dumont et al. | 530/317 |
| 4,963,367 | 10/1990 | Ecanow | 424/484 |
| 4,990,337 | 2/1991 | Kurihara et al. | 424/427 |
| 4,996,193 | 2/1991 | Hewitt et al. | 514/11 |
| 5,037,653 | 8/1991 | Dawson | 424/405 |
| 5,047,396 | 9/1991 | Orban et al. | 514/11 |
| 5,154,754 | 10/1992 | Damo et al. | 71/DIG. 1 |
| 5,342,625 | 8/1994 | Hauer | 424/455 |
| 5,525,590 | 6/1996 | Bollinger et al. | |
| 5,639,724 | 6/1997 | Cavanak | 514/11 |
| 5,741,512 | 4/1998 | Hauer | 424/450 |
| 5,756,450 | 5/1998 | Hahn et al. | 514/9 |

U.S. PATENT DOCUMENTS

| | | |
|---|---|---|
| 135171 | 3/1985 | European Pat. Off. . |
| 170623 | 2/1986 | European Pat. Off. . |
| 211258 | 2/1987 | European Pat. Off. . |
| 256856 | 2/1988 | European Pat. Off. . |
| 274431 | 7/1988 | European Pat. Off. . |
| 0 315 079 | 5/1989 | European Pat. Off. . |
| 314689 | 5/1989 | European Pat. Off. . |
| 2553661 | 4/1985 | France . |
| 3315805 | 11/1984 | Germany . |
| 024776 | 4/1985 | Japan . |
| 1249918 | 4/1985 | Japan . |
| 280435 | 4/1985 | Japan . |
| 249918 | 7/1986 | Japan . |
| 2461786 | 6/1983 | Switzerland . |
| 8634788 | 6/1983 | Switzerland . |
| 641356 | 2/1984 | Switzerland . |
| 1171125 | 11/1969 | United Kingdom . |
| 2098865 | 12/1982 | United Kingdom . |
| 2206119 | 12/1988 | United Kingdom . |
| 2209671 | 5/1989 | United Kingdom . |
| 2 211 408 | 7/1989 | United Kingdom . |
| 2211848 | 7/1989 | United Kingdom . |
| 8602264 | 4/1986 | WIPO . |
| 8701035 | 2/1987 | WIPO . |
| 8800059 | 1/1988 | WIPO . |
| WO 93/20833 | 10/1993 | WIPO . |

OTHER PUBLICATIONS

Cavanak and Sucker, Prog. Allergy vol. 38:65–72 (1986).
Ekman, S., Lipids 22:657–663 (1987).
Ritichel, et al., Pharmaceutical Research vol. 5(10): Suppl. 108 (1988).
Stupar, et al., Goldschmidt Inforwist Essein. vol. 52:22–28 (1982) translation.
Takada, 87–024776/04 (Apr. 4, 1985).
Hahn, Biodegradable Tensides (1988) (translation).
Jayakrishnan, et al., J. Soc. Cosmet, Chem. 34:335–350 (1983).
Mizushima, 86–335072/51 (Jul. 26, 1985).
Mubarak, Development and Testing of New Microemulsions (1982) (translation).
Muller, et al., Pharm. Ind. 50(11): 1301–1306 (1988) (translation).
Muller, et al., Pharm. Ind. 50(3): 370–375 (1988) (translation).
Pohler, Micro–Emulsion Gels Structural Investigations and Galenical Properties (1983) (translation).
Remington's Pharmaceutical Sciences (17th ed.). Microemulsions, Chapter 20, pp. 298–299 (1985).
Reymond, et al., Pharmaceutical Research vol. 1 5(10):673–767 (1988).
Reymond, et al., Pharmaceutical Research vol. 5(10):677–679 (1988).
Reymond, In Vitro In Vivi Model for the Absorption of Cyclosporin A (1986) (translation).
Reymond, Pharm. Res. 5, No. 10.
Ritchel, et al., Meth and Find Exp Clin Pharmacol. vol. 11(4):281–87 (1989).
Ritichel, Pharm, Res. suppl. 108 (abstract).
Takada, et al., Int. of Pharmaceutics, vol. 44:107–116 (1988).
Takada, et al., J. Pharmaceutical Research vol. 3(1):48–51 (1986).
Takada, et al., J. Pharmacobio–Dyn. vol. 11:80–87 (1988).
Takada, et al., Pharmacobio–Dyn. vol. 8:320–323 (1985).
Takada, et al., Pharmacobio–Dyn. vol. 9:156–160 (1986).
Tarr, et al., Pharmaceutical Research, vol. 6(1):40–43 (1989).
Yanagawa, et al., J. Microencapsulation 6(2):161–164 (1989).
Ziegenmeyer, et al., Acta Pharmaceutical Technologica, vol. 26(4):273–275 1980 (translation).
Ulman's Encyclopaedia of Industrial Pharmacy, Vo. A9 (1987), pp. 298–299 and 308–311.
Carrigan et al., J. Pharm. Sci. 1973, vol. 62, pp. 1476–1479.
Frazer et al., J. Physiol. (1944) vol. 103, pp. 306–310.

PHARMACEUTICAL COMPOSITIONS COMPRISING CYCLOSPORINS

This is a division of application Ser. No. 08/811,749, filed Mar. 6, 1997 now U.S. Pat. No. 5,866,159, which is a division of application Ser. No. 08/430,770, filed Apr. 27, 1995, now U.S. Pat. No. 5,741,512, which is a continuation of application Ser. No. 08/259,951, filed Jun. 15, 1994, abandoned, which is a division of application Ser. No. 07/990,734, filed Dec. 15, 1992, now U.S. Pat. No. 5,342,625, which is a continuation of application Ser. No. 07/680,211, filed Apr. 4, 1991, abandoned, which is a continuation of application Ser. No. 07/406,656, filed Sep. 13, 1989, abandoned.

The present invention relates to novel galenic formulations comprising a cyclosporin as active ingredient.

The cyclosporins comprise a class of structurally distinctive, cyclic, poly-N-methylated endecapeptides, commonly possessing pharmacological, in particular immunosuppressive, anti-inflammatory and/or anti-parasitic activity. The first of the cyclosporins to be isolated was the naturally occurring fungal metabolite Ciclosporin or Cyclosporine, also known as cyclosporin A and commercially available under the Registered Trade Mark SANDIMMUN$^R$ or SANDIMMUNE$^R$. Ciclosporin is the cyclosporin of formula A.

(A)

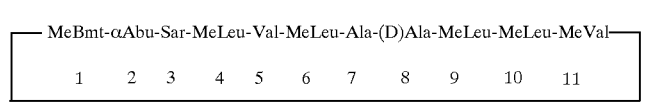

wherein -MeBmt- represents the N-methyl-(4R)-4-but-2E-en-1-yl-4-methyl-(L)threonyl residue of formula B (B)

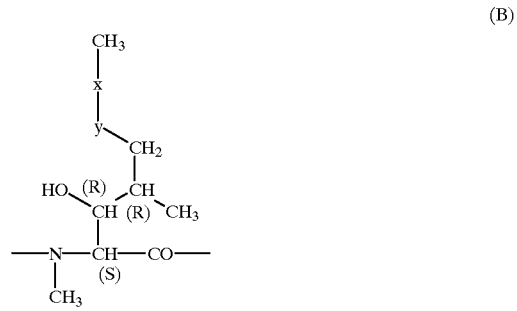

in which —x—y— is —CH=CH— (trans).

As the parent of the class Ciclosporin has so far received the most attention. The primary area of clinical investigation for Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Ciclosporin has achieved a remarkable success and reputation.

At the same time, applicability of Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific auto-immune diseases for which Ciclosporin therapy has been proposed or applied include, autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Further areas of investigation have beeni potential applicability as an anti-parasitic, in particular anti-protozoal agent, with possible uses suggested including treatment of malaria, coccidiomycosis and schistosomiasis and, yet more Recently, use as an agent for reversing or abrogating anti-neoplastic agent resistance in tumours and the like.

Since the original discovery of ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [c.f. Traber et al. 1, Helv. Chim. Acta. 60, 1247–1255 (1977); Traber et al. 2, Helv. Chim. Acta. 65 no. 162, 1655–1667 (1982); Kobel et al., Europ. J. Applied Microbiology and Biotechnology 14, 273–240 (1982); and von Wartburg et al., Progress in Allergy, 38, 28–45 (1986)], as well as various non-natural cyclosporin derivatives and artificial or synthetic cyclosporins including the so called dihydro-cyclosporins (in which the moiety —x—y— of the -MeBmt- residue (Formula B above) is saturated to give —x—y—=5—$CH_2$—$CH_2$—; derivatised cyclosporins (e.g. in which a further substituent is introduced at the a-carbon atom of the sarcosyl residue at the 3-position of the cyclosporin molecule); cyclosporins in which the -MeBmt- residue is present in isomeric form (e.g. in which the configuration across positions 6' and 7' of the -MeBmt- residue is cis rather than trans); and cyclosporins wherein variant amino acids are incorporated at specific positions within the peptide sequence, employing e.g. the total synthetic method for the production of cyclosporins developed by R. Wenger—see e.g. Traber 1, Traber 2 and Kobel loc. cit.; U.S. Pat. Nos. 4,108,985, 4,210,581 and 4,220,641; European Patent Publication Nos. 0 034 567 and 0 056 782; International Patent Publication No. WO 86/02080; Wenger 1, Transp. Proc. 15, Suppl. 1:2230 (1983); Wenger 2, Angew. Chem. Int. Ed., 24, 77 (1985); and Wenger 3, Progress in the Chemistry of Organic Natural Products 50, 123 (1986).

The class comprised by the cyclosporins is thus now very large indeed and includes, for example, [Thr]$^2$-, [Val]$^2$-,

[Nva]²- and [Nva]²- [Nva]⁵-Ciclosporin (also known as cyclosporins C,D, G and M respectively), [3-O-acyl-MeBmt]¹-Ciclosporin (also known as cyclosporin A acetate), [Dihydro-MeBmt]¹-[Val]²-Ciclosporin (also known as dihydrocyclosporin D), [(D)Fluoromethyl-Sar]³-Ciclosporin, [(D)Ser]⁸-Ciclosporin, [MeIle]¹¹-Ciclosporin, [(D)MeVal]¹¹-Ciclosporin (also known as cyclosporin H), [MeAla]⁶-Ciclosporin, [(D)Pro]³-Ciclosporin and so on.

[In accordance with now conventional nomenclature for cyclosporins, these are defined by reference to the structure of Ciclosporin (i.e. Cyclosporin A). This is done by first indicating the amino acid residues present which differ from those present in Ciclosporin (e.g. "[(D)Pro]³" to indicate that the cyclosporin in question has a -(D)Pro- rather than -Sar- residue at the 3-position) and then applying the term "Ciclosporin" to characterise remaining residues which are identical to those present in Ciclosporin. Individual residues are numbered starting with the residue -MeBmt- or -dihydroMeBmt- in position 1.]

Very many of these further cyclosporins exhibit comparable pharmaceutical utility to Ciclosporin or more specific utility, for example activity particularly in reversing tumor resistance to cytostatic therapy, and proposals for their application as therapeutic agents abound in the literature.

Despite the very major contribution which Ciclosporin has made, in particular to the areas of organ transplant and the therapy of autoimmune diseases, difficulties encountered in providing more effective and convenient means of administration as well as the reported occurrence of undesirable side reactions, in particular nephrotoxic reaction, have been obvious serious impediments to its wider use or application. The cyclosporins are characteristically highly hydrophobic. Proposed liquid formulations, e.g. for oral administration of cyclosporins, have hitherto been based primarily on the use of ethanol and oils or similar excipients as carrier media. Thus the commercially available Ciclosporin drink-solution employs ethanol and olive oil as carrier medium in conjunction with labrafil as a surfactant—see e.g. U.S. Pat. No. 4,388,307. Use of the drink-solution and similar compositions as proposed in the art is however accompanied by a variety of difficulties.

First, the necessity to use oils or oil based carriers may lend the preparations an unpleasant taste or otherwise reduce palatability, in particular for the purposes of long-term therapy. These effects can be masked by presentation in gelatin capsule form. However, in order to maintain the cyclosporin in solution, the ethanol content has to be kept high. Evaporation of the ethanol, e.g. from capsules or from other forms, e.g. when opened, results in the development of a cyclosporin precipitate. Where such compositions are presented in e.g. soft gelatin encapsulated form, this particular difficulty necessitates packaging of the encapsulated product in an air-tight compartment, for example an air-tight blister or aluminium-foil blister-package. This in turn renders the product both bulky and more expensive to produce. The storage characteristics of formulations as aforesaid are far from ideal.

Bioavailability levels achieved using existing oral cyclosporin dosage systems are also low and exhibit wide variation between individuals, individual patient types and even for single individuals at different times during the course of therapy. Thus reports in the literature indicate that currently available therapy employing the commercially available Ciclosporin drink solution provides an average absolute bioavailability of ca. 30% only, with marked variation between individual groups, e.g. between liver (relatively low bioavailability) and bone-narrow (relatively high bioavailability) transplant recipients. Reported variation in bioavailability between subjects has varied from anything between one or a few percent for some patients to as much as 90% or more for others. And as already noted, marked change in bioavailability for individuals with time is frequently observed.

To achieve effective immunosuppressive therapy, cyclosporin blood or blood serum levels have to be maintained within in a specified range. The required range can in turn vary, depending on the particular condition being treated, e.g. whether therapy is to prevent transplant rejection or for the control of an autoimmune disease, and on whether or not alternative immunosuppressive therapy is employed concomitantly with cyclosporin therapy. Because of the wide variations in bioavailability levels achieved with conventional dosage forms, daily dosages needed to achieve required blood serum levels will also vary considerably from individual to individual and even for a single individual. For this reason it is necessary to monitor blood/blood-serum levels of patients receiving cyclosporin therapy at regular and frequent intervals. Monitoring of blood/blood-serum levels, which is generally performed by RIA or equivalent immunoassay technique, e.g. employing monoclonal antibody based technology, has to be carried out on a regular basis. This is inevitably time consuming and inconvenient and adds substantially to the overall cost of therapy.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty which has however remained is the inherent insolubility of the cyclosporins, e.g. Ciclosporin, in aqueous media and hence provision of a dosage from which can contain cyclosporins in sufficiently high concentration to permit convenient use and yet meet the required criteria in terms of bioavailability, e.g. enabling effective resorption from the stomach or gut lumen and achievement of consistent and appropriately high blood/blood-serum levels.

The particular difficulties encountered in relation to oral dosaging with cyclosporins have inevitably led to restrictions in the use of cyclosporin therapy for the treatment of relatively less severe or endangering disease conditions. A particular area of difficulty in this respect has been the adoption of cyclosporin therapy in the treatment of autoimmune diseases and other conditions affecting the skin, for example for the treatment of atopic dermatitis and psoriasis and, as also widely proposed in the art, for hair growth stimulation, e.g. in the treatment of alopecia due to ageing or disease.

Thus while oral Ciclosporin therapy has shown that the drug is of considerable potential benefit to patients suffering e.g. from psoriasis, the risk of side-reaction following oral therapy has prevented common use. Various proposals have been made in the art for application of cyclosporins, e.g. Ciclosporin, in topical form and a number of topical delivery systems have been described. Attempts at topical application have however failed to provide any demonstrably effective therapy. A means of topical application providing effective dermal delivery and useful, e.g. for the treatment of psoriasis, would effectively make cyclosporin therapy available to, what is, a major patient population at need.

By the present invention there are provided novel cyclosporin galenic formulations in the form of a microemulsion pre-concentrate and/or based on the use of particular solvent media as hereinafter defined, which meet or substantially reduce difficulties in cyclosporin, e.g Ciclosporin, therapy hitherto encountered in the art. In particular it has been found that the compositions of the invention permit the preparation of solid, semi-solid and liquid compositions containing a cyclosporin in sufficiently high concentration to permit, e.g. convenient oral administration, while at the same time achieving improved efficacy, e.g. in terms of bioavailability characteristics.

More particularly it has been found that compositons in accordance with the present invention enable effective cyclosporin dosaging with concomitant enhancement of resorption/bioavailability levels, as well as reduced variability in resorption/bioavailability levels achieved both for individual patients receiving cyclosporin therapy as well as between individuals. By application of the teachings of the present invention cyclosporin dosage forms are obtainable providing reduced variablility in achieved cyclosporin blood/blood serum levels between dosages for individual patients as well as between individuals/individual patient groups. The invention thus enables reduction of cyclosporin dosage levels required to achieve effective therapy. In addition it permits closer standardisation as well as optimisation of on-going daily dosage requirements for individual subjects receiving cyclosporin therapy as well as for groups of patients undergoing equivalent therapy.

By closer standardisation of individual patient dosaging rate and blood/blood-serum level response, as well as dosaging and response parameters for patient groups, monitoring requirements may be reduced, thus substantially reducing the cost of therapy.

By reduction of required cyclosporin dosaging/standardisation of achieved bio-availability characteristics, the present invention also offers a means permitting reduction in the occurrence of undesirable side-effects, in particular nephrotoxic reaction, in patients undergoing cyclosporin therapy.

In addition, the present invention enables the preparation of compositions which are non-alkanol based, e.g. which may be free or substantially free of ethanol. Such compositions avoid stability and related processing difficulties as hereinbefore discussed, inherent to known alkanolic compositions. The invention thus provides inter al. compositions which are better adapted, e.g. for presentation in capsule, e.g. hard or soft gelatin capsule form and/or which eliminate or substantially reduce packaging difficulties, for example as hereinbefore discussed, e.g. for soft gelatin encapsulated forms.

In relation to topical application, the present invention further enables the preparation of novel galenical formulations comprising a cyclosporin, e.g. Ciclosporin, as active ingredient and permitting improved treatment for autoimmune diseases affecting the skin, in particular, of dermatological disease involving morbid proliferation and/or keratinisation of the epidermis, especially of psoriasis and atopic dermatosis. Topically applicable compositions in accordance with the invention are also of use in the treatment of alopecia, e.g. for use in the promotion of hair growth.

In a first aspect, the present invention specifically provides pharmaceutical compositions comprising a cyclosporin as active ingredient, which compositions are in the form of a "microemulsion pre-concentrate".

By the term "microemulsion pre-concentrate" as used herein is meant a system capable on contacting with, e.g. addition to, water of providing a microemulsion. The term microemulsion as used herein is used in its conventionally accepted sense as a non-opaque or substantially non-opaque colloidal dispersion comprising water and organic components including hydrophobic (lipophilic) organic components. Microemulsions are identifiable as possessing one or more of the following characteristics. They are formed spontaneously or substantially spontaneously when their components are brought into contact, that is without substantial energy supply, e.g. in the absence of heating or the use of high shear equipment or other substantial agitation. They exhibit thermodynamic stability. They are monophasic. They are substantially non-opaque, i.e. are transparent or opalescent when viewed by optical microscopic means. In their undisturbed state they are optically isotropic, though an anisotropic structure may be observable using e.g. x-ray technique.

Microemulsions comprise a dispersed or particulate (droplet) phase, the particles of which are of a size less than 2,000 Å, hence their optical transparency. The particles of a microemulsion may be spherical, though other structures are feasible, e.g. liquid crystals with lamellar, hexagonal or isotropic symmetries. Generally, micro-emulsions comprise droplets or particles having a maximum dimension (e.g. diameter) of less than 1,500 Å, e.g. typically from 100 to 1,000 Å.

[For further discussion of the characteristics of microemulsions see, e.g. Rosof, Progress in Surface and Membrane Science, 12, 405 et seq. Academic Press (1975); Friberg, Dispersion Science and Technology, 6 (3), 317 et seq. (1985); and Muller et al. Pharm. Ind., 50 (3), 370 et seq. (1988)].

From the foregoing it will be understood that the "microemulsion pre-concentrates" of the invention are galenic systems comprising a cyclosporin as active ingredient capable of forming a microemulsion, spontaneously or substantially spontaneously on contact with water alone.

Pharmaceutical "microemulsion pre-concentrate" compositions comprising cyclosporins as active ingredient are novel. Accordingly in one aspect the present invention provides:

A) A pharmaceutical composition comprising a cyclosporin as active ingredient, which composition is a "microemulsion pre-concentrate".

(The term "pharmaceutical composition" as used herein and in the accompanying claims is to be understood as defining compositions of which the individual components or ingredients are themselves pharmaceutically acceptable, e.g. where oral administration is foreseen, acceptable for oral use and, where topical administration is foreseen, topically acceptable.)

In addition to the cyclosporin active ingredient, the "microemulsion pre-concentrate" compositions of the invention will appropriately comprise:

1) a hydrophilic phase;
2) a lipophilic phase; and
3) a surfactant.

The cyclosporin is carried in the lipophilic phase. Suitably both the hydrophilic and lipophilic phases will serve as carrier medium.

"Microemulsion pre-concentrates" of the invention are of a type providing o/w (oil-in-water) microemulsions. As will be appreciated however, compositions in accordance with (A) may contain minor quantities of water or otherwise exhibit fine structural features characteristic of microemulsions, e.g. of o/w or w/o (water-in-oil) type. The term "microemulsion pre-concentrate" as used herein is accordingly to be understood as embracing such possibilities.

Microemulsions obtained on contacting the "microemulsion pre-concentrate" compositions of the invention with water or other aqueous medium exhibit thermodynamic stability, that is they will remain stable at ambient temperatures, e.g. without clouding or regular emulsion size droplet formation or precipitation, over prolonged periods of time. [It will of course be understood that, to obtain a microemulsion, adequate water will be required. While the upper limit of dilution is not critical, a dilution of 1:1, e.g. 1:5 p.p.w. ("microemulsion pre-concentrate": $H_2O$) or more will generally be appropriate.] Preferably, on contacting with water, the "microemulsion pre-concentrate" compositions of the invention are capable of providing microemulsions which remain stable at ambient temperatures, e.g. as evidenced by absence of any optically observable clouding or precipitation, over periods of at least 2 hours, more preferably at least 4 hours, most preferably at least 12 to 24 hours. Microemulsions obtainable from "microemulsion pre-concentrates" of the invention, e.g. at dilutions as indicated above, will preferably have an average particle size of less than about 1,500 Å, more preferably of less than about 1,000 or 1,100 Å, e.g. down to about 150 or 200 Å.

Especially preferred in accordance with the present invention are compositions as defined under (A) in which the hydrophilic phase comprises:

1.1. A pharmaceutically acceptable $C_{1-5}$ alkyl or tetrahydrofurfuryl di- or partial-ether of a low molecular weight mono- or poly-oxy-alkanediol; or 1.2. 1,2-propyleneglycol.

Suitable components (1.1.) are, e.g. di- or partial-, especially partial-, -ethers of mono- or poly-, especially mono- or di-, -oxy-alkanediols comprising from 2 to 12, especially 4 carbon atoms. Preferably the mono- or poly-oxy-alkanediol moiety is straight-chained. Especially suitable for use in accordance with the invention are di- or partial-ethers of formula I $$R_1-[O-(CH_2)_2]_x-OR_2 \quad (I)$$

wherein $R_1$ is $C_{1-5}$ alkyl or tetrahydrofurfuryl, $R_2$ is hydrogen, $C_{1-5}$ alkyl or tetrahydrofurfuryl, and x is an integer of from 1 to 6, especially from 1 to 4, most especially about 2.

Particularly preferred for use in accordance with the invention are partial ethers as defined above, e.g. products of formula I, wherein $R_2$ is hydrogen.

$C_{1-5}$ alkyl moieties in the above defined ethers may be branched or straight chain, e.g. including methyl, ethyl, n-propyl, i-propyl, n-butyl and t-butyl groups.

Such ethers are known products and commercially available or may be produced analogously to the known products. Especially preferred products of formula I for use in relation to the present invention are those known and commercially available under the trade names Transcutol and Glycofurol.

Transcutol is the compound diethyleneglycol monoethyl ether of formula I, wherein $R_1=C_2H_5$, $R_2=H$ and x=2.

Glycofurol, also known as tetrahydrofurfuryl alcohol polyethylene glycol ether or α-(tetrahydrofuranyl)-ω-hydroxypoly(oxy-1,2-ethanediyl) has the formula I wherein $R_1=$

$R_2=H$ and x has an average value of from 1 to 2. It has an average molecular weight of ca. 190; a b.p. of from ca. 80–100° C. (at $40N/m^2$), a density of ca. 1.070–1.090 $g/cm^3$ (at 20° C.); a hydroxy value of ca. 300–400; a refractive index of ca. 1.4545 (sodium D line, 589 mm) (at 40° C.); and a viscosity of ca. 8–18 mN $s/m^2$ (at 20°). [c.f. "Handbook of Pharmaceutical Excipients, published by American Pharmaceutical Association/The Pharmaceutical Society of Great Briatin (1986), p. 127 and Fiedler, "Lexikon der Hilfstoffe", 3rd edition (1989), p. 577.1

The precise properties of Glycofurol vary according to relative purity. Thus lower quality grades contain significant amounts of tetrahydrofurfuryl alcohol and other impurities. For the purposes of the present invention Glycofurol 75, designating a product meeting the above physical data and for which the fraction having the formula I above in which x=1–2 amounts to a minimum of 95%, is preferred.

Use of components defined under (1.1.) and (1.2.) above has in particular been found to provide compositions in accordance with (A) in which the hydrophilic phase is especially well suited as cyclosporin carrier medium, e.g. in which the hydrophilic phase enables cyclosporin-loading of the composition, adequate for convenient therapeutic dosaging, e.g. for oral administration.

Compositions in accordance with (A) comprising components as defined under (1.1.) and/or (1.2.) as hydrophilic phase may of course additionally include one or more further ingredients as hydrophilic phase component. Preferably however any additional components will comprise materials in which the cyclosporin active ingredient is sufficiently soluble, such that the efficacy of the hydrophilic phase as cyclosporin carrier medium is not materially impaired. Examples of possible additional hydrophilic phase components are lower (e.g. $C_{1-5}$) alkanols, in particular ethanol.

While, however, use of alkanols, e.g. ethanol, as hydrophilic phase component is contemplated by the present invention, for reasons hereinbefore discussed, this will be generally less preferred. Preferably, compositions as defined under (A) will be non-alkanol-based, i.e. will not comprise an alkanol as a predominant hydrophilic phase component. Suitably the hydrophilic phase comprises less than 50%, more preferably less than 25%, most preferably less than 10% by weight alkanolic components. Most suitably, the hydrophilic phase will be free or substantially free of alkanolic components, i.e. comprise less than 5%, preferably less than 2%, e.g. from 0 to 1% alkanolic components. By "alkanol" is meant, in particular, $C_{1-5}$ alkanols, especially ethanol.

In an especially preferred embodiment the hydrophilic phase of compositions defined under (A) will consist or consist essentially of components as defined under (1.1.) or (1.2.) above, in particular Transcutol, Glycofurol and/or 1,2-propylene glycol. Most suitably they will consist or consist essentially of either components (1.1.) or component (1.2.).

Compositions in accordance with (A) comprising a component (1.1), especially Glycofurol, are of particular interest in that they are well adapted for presentation in soft gelatin encapsulated form. Such compositions have, in accordance with the invention, also been found to exhibit surprisingly advantageous stability, e.g. as evidenced in long-term stability tests at normal and elevated temperatures. Such compositions are thus particularly well suited to meet difficulties commonly encountered in transport and storage of drug products, including long term storage at the user end, e.g. in hospitals, clinics and like facilities.

Compositions defined under (A) additionally comprise a lipophilic phase (2).

Suitable components for use as lipophilic phase include any pharmaceutically acceptable solvent which is non-miscible with the selected hydrophilic phase, e.g. as defined under (1.1.) or (1.2.). Such solvents will appropriately be devoid or substantially devoid of surfactant function. Especially suitable components for use as lipophilic phase components (2) are, e.g.:

Fatty acid triglycerides, preferably medium chain fatty acid triglycerides. Especially suitable are neutral oils, e.g. neutral plant oils, in particular fractionated coconut oils such as known and commercially available under the trade name Miglyol (c.f. Fiedler, loc. cit. pp. 808–809), including the products:

Miglyol 810: a fractionated coconut oil comprising caprylic-capric acid triglycerides and having a molecular weight: ca. 520. Fatty acid composition=$C_6$ max. 2%, $C_8$ ca. 65–75%, $C_{10}$ ca. 25–35%, $C_{12}$ max. 2%; acid no. ca.=0.1; saponification no.=ca. 340–360; iodine no.=max. 1;

Miglyol 812: a fractionated coconut oil comprising caprylic-capric acid triglycerides and having a molecular weight=ca. 520. Fatty acid composition=$C_6$ max. ca. 3%, Cs ca. 50–65%, $C_{10}$ ca. 30–45%, $C_{12}$ max. 5%; acid no.=ca. 0.1; saponification no.=ca. 330–345; iodine no.=max. 1;

Miglyol 818: a caprylic-capric-linoleic acid triglyceride having a molecular weight=ca. 510. Fatty acid composition= $C_6$ max. 3, $C_8$ ca. 45–60, $C_{10}$ ca. 25–40, $C_{12}$ ca. 2–5, $C_{18:2}$ ca. 4–6; acid no.=max. 0.2; saponification no.=ca. 315–335, iodine no.=max. 10; and Captex 355($^1$) a caprylic-capric acid triglyceride. Fatty acid content=caproic ca. 2%, caprylic ca. 55%, capric ca. 42%. Acid no.=max. 0.1; saponification no.=ca. 325–340; iodine no.=max. 0.5.

Also suitable are caprylic-capric acid triglycerides such as known and commercially available under the trade name Myritol (c.f. Fiedler loc. cit., p. 834) including the product Myritol 813 which has an acid no.=max. 1, a saponification no.=ca. 340–350 and an iodine no.=ca. 0.5.

Further suitable products of this class are Capmul MCT ($^1$), Captex 300($^1$) and Captex 800($^1$), Neobee M5($^2$) and Mazol 1400($^3$).

[(1)=Capital City Products, PO.Box 569, Columbus, Ohio, USA. (2)=Stepan, PVO Dept., 100 West Hunter Ave., Maywood, N.J. 07607, USA. (3)=Mazer Chemicals, 3938 Porett Drive, Gurnee, Ill., USA).]

Especially preferred as lipophilic phase component is the product Miglyol 812.

Compositions in accordance with the invention defined under (A) further comprise a pharmaceutically acceptable surfactant (3). The surfactant component may comprise (3.1.) hydrophilic or (3.2.) lipophilic surfactants, or mixtures thereof. Especially preferred are non-ionic hydrophilic and non-ionic lipophilic surfactants. Examples of suitable hydrophilic surfactants for use as surfactant components are e.g.:

3.1.1. Reaction products of natural or hydrogenated vegetable oils and ethylene glycol, i.e. polyoxyethylene glycolated natural or hydrogenated vegetable oils, for example polyoxyethylene glycolated natural or hydrogenated castor oils. Such products may be obtained in known manner, e.g. by reaction of a natural or hydrogenated castor oil or fractions thereof with ethylene oxide, e.g. in a molar ratio of from about 1:35 to about 1:60, with optional removal of free polyethyleneglycol components from the product, e.g. in accordance with the methods disclosed in German Auslegeschriften 1,182,388 and 1,518,819. Especially suitable are the various tensides available under the trade name Cremophor. Particularly suitable are the products Cremophor RH 40 having a saponification no. ca. 50–60, an acid no.=<1, an iodine no.=<1, a water content (Fischer)=<2%, an $n_D^{60}$=ca. 1,453–1,457 and an HLB=ca. 14–16; Cremophor RH 60 having a saponification no.=ca. 40–50, an acid No.=<1, an iodine no.=<1, a water content (Fischer)=ca. 4.5–5.5%, an $n_D^{25}$=ca. 1.453–1,457 and an HLB=ca. 15–17; and Cremophor EL having a molecular weight (by steam osmometry)=ca. 1630, a saponification no.=ca. 65–70, an acid no.=ca. 2, an iodine no.=ca. 28–32 and an $n_D^{25}$=ca. 1.471 (c.f. Fiedler loc. cit. pp. 326–327). Also suitable for use in this category are the various tensides available under the trade name Nilckol, e.g. Nikkol HCO-60. The said product Nikkol HCO-60 is a reaction product of hydrogenated castor oil and ethylene oxide exhibiting the following characteristics: Acid no.=ca. 0.3; Saponification no.=ca. 47.4; Hydroxy value=ca. 42.5; pH (5%)=ca. 4.6; Color APHA=ca. 40; m.p.=ca. 36.0° C.; Freezing point=ca. 32.4° C.; $H_2O$ content (%, KF)=ca. 0.03;

3.1.2. Polyoxyethylene-sorbitan-fatty acid esters e.g. mono- and trilauryl, palmityl, stearyl and oleyl esters e.g. of the type known and commercially available under the trade name Tween (c.f. Fiedler, loc. cit. pp. 1300–1304) including the products Tween 20 [polyoxyethylene(20)sorbitanmonolaurate],
40 [polyoxyethylene(20)sorbitanmonopalmitate],
60 [polyoxyethylene(20)sorbitanmonostearate],
80 [polyoxyethylene(20)sorbitanmonooleate],
65 [polyoxyethylene(20)sorbitantristearate],
85 [polyoxyethylene(20)sorbitantrioleate],
21 [polyoxyethylene(4)sorbitanmonolaurate],
61 [polyoxyethylene(4)sorbitanmonostearate], and
81 [polyoxyethylene(5)sorbitanmonooleate].

Especially preferred products of this class for use in the compositions of the invention are the above products Tween 40 and Tween 80;

3.1.3. Polyoxyethylene fatty acid esters, for example polyoxyethylene stearic acid esters of the type known and commercially available under the trade name Myrj (c.f. Fiedler, loc. cit., p. 834) as well as polyoxyethylene fatty acid esters known and commercially available under the trade name Cetiol HE. (c.f.

Fiedler, loc. cit., p. 284); an especially preferred product of this class for use in the compositions of the invention is the product Myrj 52 having a $D^{25}$=ca. 1.1., m.p.=ca. 40–44° C., an HLB=ca. 16.9., an acid no.=ca. 0–1 and a saponification no.=ca. 25–35;

3.1.4. Polyoxyethylene-polyoxypropylene co-polymers, e.g. of the type known and commercially available under the trade names Pluronic and Emkalyx (c.f. Fiedler, loc. cit., pp. 956–958). An especially preferred product of this class for use in the compositions of the invention is the product Pluronic F68;

3.1.5. Polyoxyethylene-polyoxypropylene block co-polymers, e.g. of the type known and commercially available under the trade name Poloxamer (c.f. Fiedler, loc. cit., pp. 959). An especially suitable product of this class for use in the compositions of the invention is the product Poloxamer 188;

3.1.6. Dioctylsuccinate, dioctylsodiumsulfosuccinate, di-[2-ethylhexyl]-succinate or sodium lauryl sulfate;

3.1.7. Phospholipids, in particular lecithins (c.f. Fiedler, loc. cit., pp. 731–733). Lecithins suitable for use in the compositions of the invention include, in particular, soya bean lecithins;

3.1.8. Propylene glycol mono- and di-fatty acid esters such as propylene glycol dicaprylate, propylene glycol dilaurate, propylene glycol hydroxystearate, propylene glycol isostearate, propylene glycol laurate, propylene glycol ricinoleate, propylene glycol stearate and so forth (c.f. Fiedler, loc. cit., pp. 1013 et seq.). Especially preferred is propylene glycol caprylic-capric acid diester as known and commercially available under the trade name Miglyol 840 (c.f. Fiedler, loc. cit., p. 809). Miglyol 840 has a fatty acid content=$C_6$ max. ca. 3%, $C_8$ ca. 65–80%, $C_{10}$ ca. 15–30%, $C_{12}$ max. 3%. Acid no.=max. 0.1, iodine no.=ca. 320–340, iodine no.=max. 1; and 3.1.9. Bile salts, e.g. alkali metal salts, for example sodium taurocholate.

Examples of suitable lipophilic surfactants for use as surfactant component are, e.g.:

3.2.1. Trans-esterification products of natural vegetable oil triglycerides and polyalkylene polyols. Such trans-esterification products are known from the art and may be obtained e.g. in accordance with the general procedures described in U.S. Pat. No. 3,288,824. They include trans-esterification products of various natural (e.g. non-hydrogenated) vegetable oils for example, maize oil, kernel oil, almond oil, ground nut oil, olive oil and palm oil and mixtures thereof with polyethylene glycols, in particular polyethylene glycols having an average molecular weight of from 200 to 800. Preferred are products obtained by trans-esterification of 2 molar parts of a natural vegetable oil triglyceride with one molar part of polyethylene glycol (e.g. having an average molecular weight of from 200 to 800). Various forms of trans-esterification product of the class defined are known and commercially available under the trade name Labrafil (see Fiedler, loc. cit., 707]. Especially useful as components of the compositions of the invention are the products: Labrafil M 1944 CS, a trans-esterification product of kernel oil and polyethylene glycol having an acid no. ca.=2, a saponification no. ca. 145–175 and an iodine no.=ca. 60–90; and Labrafil M 2130 CS, a trans-esterification product of a $C_{12}$- to $C_{18}$- glyceride and polyethylene glycol having a melting point=ca. 35–40° C., an acid no.=<2, a saponification no.=ca. 185–200 and an iodine no. <3;

3.2.2. Mono-, di- and mono/di-glycerides, especially esterification products of caprylic or capric acid with glycerol. Preferred products of this class are e.g. those comprising or consisting mainly or essentially of caprylic/capric acid mono- and di-glycerides such as are commercially available under the trade name Imwitor (c.f. loc. cit., pp. 645). A particularly suitable product of this class for use in the compositions of the invention is the product Imwitor 742, which is the esterification product of a mixture of ca. 60 p.p.w. caprylic acid and ca. 40 p.p.w. capric acid with glycerol. Imwitor 742 is typically a yellowish crystalline mass, liquid at ca. 26° C.; acid no.=max. 2; iodine no.=max. 1; saponification no.=ca. 235–275: X monoglycerides=ca. 40–50%; free glycerol=max. 2%; m.p.=ca. 24–26° C.; unsaponifiables=0.3% max.; peroxide no.=max. 1;

3.2.3. Sorbitan fatty acid esters e.g. of the type known and commercially available under the trade name Span, for example including sorbitan-monolauryl, -monopalmityl, -monostearyl, -tristearyl, -monooleyl and -trioleyl esters—(c.f. Fiedler, loc. cit., pp. 1139–1140);

3.2.4. Pentaerythritol fatty acid esters and polyalkylene glycol ethers, for example pentaerythrite- -dioleate, -distearate, -monolaurate, -polyglycol ether and -monostearate as well as pentaerythrite-fatty acid esters (c.f. Fiedler, loc. cit. pp. 923–924);

3.2.5. Monoglycerides, e.g. glycerol monooleate, glycerol monopalmitate and glycerol monostearate, for example as known and commercially available under the trade names Myvatex, Myvaplex and Myverol (c.f. Fiedler, loc. cit., pp. 836), and acetylated, e.g. mono-and di-acetylated monoglycerides, for example as known and commercially available under the trade name Myvacet (c.f. Fiedler, loc. cit., pp. 835);

3.2.6. Glycerol triacetate or (1,2,3)-triacetin (c.f. Fiedler, loc. cit., pp. 952); and 3.2.7. Sterols and derivatives thereof, for example cholesterols and derivatives thereof, in particular phytosterols, e.g. products comprising sitosterol, campesterol or stigmasterol, and ethylene oxide adducts thereof, for example soya sterols and derivatives thereof, such as known under the trade name Generol (c.f. Fiedler loc. cit., p.p. 554 and 555) in particular the products Generol 122, 122 E5, 122 E10, and 122 E25.

Compositions as defined under (A) above include systems comprising either a single surfactant or mixture of surfactants,. e.g. comprising a first surfactant and one or more co-surfactants. Surfactant and co-surfactant combinations may be selected, e.g. from any of the surfactant types indicated under (3.1.1.) to (3.2.7.) above.

When the hydrophilic phase comprises a di- or partial-ether as defined under (1.1) above, in particular Transcutol or Glycofurol, use of a single surfactant will generally be sufficient, though co-surfactants may be added if desired, e.g. to further improve stability characteristics. When 1,2-propylene glycol is employed as sole or principle hydrophilic phase component, the use of at least two surfactants, i.e. a surfactant and co-surfactant, will generally be required. Compositions as defined under (A) comprising 1,2-propylene glycol as hydrophilic phase thus suitably comprise both a surfactant and a co-surfactant.

Surfactants as defined under (3.1.1.), (3.1.3.), (3.1.7), (3.2.2.) and (3.2.5.) above are of particular interest for use in compositions as defined under (A). Especially suitable surfactant/co-surfactant combinations are hydrophilic/lipophilic surfactant combinations, e.g. combinations of surfactants in accordance with (3.1.1.) with surfactants in accordance with (3.2.5.).

When the surfactant comprises an effective solvent for the cyclosporin active ingredient, as in the case e.g. of surfactants or mixtures of surfactants under (3.1.1.) to (3.2.7.) above, it may be incorporated into compositions as defined under (A), not only as surfactant, but in excess as an additional carrier or co-solvent phase, i.e. as part of the hydrophilic or lipophilic phase.

Compositions in accordance with (A) above may also comprise:

4. A thickening agent.

Suitable thickening agents may be of those known and-employed in the art, including, e.g. pharmaceutically acceptable polymeric materials and inorganic thickening agents, for example of the following types:

4.1. Polyacrylate and polyacrylate co-polymer resins, for example poly-acrylic acid and poly-acrylic acid/methacrylic acid resins, such as known and commercially available under the trade name Carbopol (c.f. Fiedler, loc. cit., pp. 254–256), in particular the products Carbopol 934, 940 and 941, and Eudragit (c.f. Fiedler, loc. cit., pp. 486–487), in particular the products Eudragit E, L, S, RL and RS and, most especially, the products Eudragit E, L and S;

4.2. Celluloses and cellulose derivatives including: alkyl celluloses, e.g. methyl-, ethyl- and propyl-celluloses;

hydroxyalkyl-celluloses, e.g. hydroxypropyl-celluloses and hydroxypropylalkyl-celluloses such as hydroxypropyl-methyl-celluloses; acylated celluloses, e.g. cellulose-acetates, cellulose-acetatephthallates, cellulose-acetatesuccinates and hydroxypropylmethyl-cellulose phthallates; and salts thereof such as sodium-carboxymethyl-celluloses. Examples of such products suitable for use in accordance with the present invention are those known and commercially available, e.g. under the trade names Klucel and Methocel (c.f. Fiedler, loc. cit., pp. 688 and 790), in particular the products Klucel LF, MF, GF and HF and Methocel K 100, K 15M, K 100M, E 5M, E 15, E 15M and E 100M;

4.3. Polyvinylpyrrolidones, including for example poly-N-vinylpyrrolidones and vinylpyrrolidone co-polymers such as vinylpyrrolidone-vinylacetate co-polymers. Examples of such compounds suitable for use in accordance with the present invention are those known and commercially available, e.g. under the trade name Kollidon (or, in the USA, Povidone) (c.f. Fiedler, loc. cit., pp. 694–696), in particular the products Kollidon 30 and 90;

4.4. Polyvinyl resins, e.g. including polyvinylacetates and alcohols, as well as other polymeric materials including gum traganth, gum arabicum, alginates, e.g. alginic acid, and salts thereof, e.g. sodium alginates;

4.5. Inorganic thickening agents such as atapulgite, bentonite and silicates including hydrophilic silicon dioxide products, e.g. alkylated (for example methylated) silica gels, in particular colloidal silicon dioxide products as known and commercially available under the trade name Aerosil [c.f. Handbook of Pharmaceutical Excipients, loc. cit., p.p. 253–256] in particular the products Aerosil 130, 200, 300, 380, 0, OX 50, TT 600, MOX 80, MOX 170, LK 84 and the methylated Aerosil R 972.

In the case of compositions in accordance with (A) which are intended for oral administration, such thickening agents may be included, e.g. to provide a sustained release effect. However, where oral administration is intended, the use of thickening agents as aforesaid will generally not be required and is generally less preferred. Use of thickening agents is, on the other hand, indicated, e.g. where topical application is foreseen.

Compositions in accordance with (A) above may also include one or more further ingredients in particular diluents, anti-oxidants [e.g. ascorbyl palmitate, butyl hydroxy anisole (BHA), butyl hydroxy toluene (BHT) and tocopherols, e.g. α-tocopherol (vitamin E)], flavouring agents and so forth. Use of an anti-oxidant, in particular a tocopherol, is particularly advantageous.

While it is foreseen, especially where oral administration is contemplated, that compositions in accordance with the invention as defined under (A) should comprise end dosage forms for administration as such, the present invention also provides phatmaceocical compositions comprising a cyclosporin as active ingredient and which are themselves microemulsions. Thus where oral administration is practiced, microemulsions obtained, e.g. by diluting a "microemulsion pre-concentrate" as defined under (A) with water or other aqueous medium may be employed as formulations for drinking. Similarly, where topical application is foreseen, compositions comprising a hydrocolloid thickening agent, e.g. as set forth under (4.2.) or (4.4.) above will suitably also comprise water, thus providing an aqueous microemulsion in gel, paste, cream or like form. Such compositions are also new. Accordingly in a yet further aspect the present invention provides:

B) A pharmaceutical composition which is a microemulsion and comprises a cyclosporin as active ingredient.

Compositions as defined under (B) may comprise any of components (1) to (3) as hereinbefore described in relation to compositions as defined under (A) and water. Compositions (B) are o/w microemulsions. Preferably they will exhibit stability characteristics as hereinbefore described in relation to microemulsions obtainable from compositions defined under (A).

In accordance with the present invention it has further been found that use of di- or partial-ethers as defined under (1.1.) as carrier media is quite generally advantageous for the preparation of pharmaceutical compositions comprising cyclosporins, not only in relation to the preparation of "microemulsion pre-concentrate" and microemulsion formulations as hereinbefore described. Thus use of such ethers as components of other oral and, in particular, topical delivery systems is surprisingly found of itself to meet difficulties hitherto encountered in the art as hereinbefore described. Such compositions are also new. Accordingly in a yet further embodiment the present invention also provides:

C) A pharmaceutical composition comprising a cyclosporin as active ingredient, together with a pharmaceutically acceptable $C_{1-5}$ alkyl or tetrahydrofurfuryl di- or partial-ether of a low molecular weight mono- or poly-oxy-alkane diol.

Preferred ether components for use in compositions as defined under (C) above are as hereinbefore described in relation to (1.1.), the products Transcutol and Glycofurol being especially preferred. Compositions in accordance with (C) suitably contain one or more further ingredients, e.g. surfactants, co-solvents or thickening agents.

In particular, compositions as defined under (C) will suitably also comprise a pharmaceutically acceptable hydrophilic surfactant especially a non-ionic hydrophilic surfactant. Suitable hydrophilic surfactant components are any of those hereinbefore described under (3.1.1.) to (3.1.9.).

Compositions as defined under (C) also suitably comprise a pharmaceutically acceptable lipophilic surfactant either as a surfactant or as a co-solvent, or a pharmaceutically acceptable co-solvent. Suitable co-solvent/lipophilic surfactant components are any of those hereinbefore described under (2) and (3.2.1.) to (3.2.7.).

Compositions in accordance with (C) include forms other than as defined under (A) and (B), for example solutions, suspensions, dispersions regular emulsions and the like. In partiuclar compositions in accordance with (C) which additionally comprise a surfactant or both a surfactant and a co-solvent include, for example, emulsion pre-concentrates (i.e. compositions which, on contacting with water, provide regular emulsions—as opposed to microemulsions—of the o/w or w/o type), and regular emulsions of both hydrophilic/lipophilic and lipophilic/hydrophilic type. In the case of formulations, e.g. for drinking or for topical application, they will in particular also include aqueous emulsions of o/w or w/o type. In general emulsion pre-concentrates giving o/w emulsions and (ii) o/w emulsions as such will be preferred, in particular where oral administration is contemplated.

Compositions as defined under (C) may further comprise a pharmaceutically acceptable thickening agent, suitable thickening agents being any of those hereinbefore described under (4.1.) to (4.5.).

Compositions in accordance with (C) may also comprise further additives, e.g. preserving and flavouring agents etc . . . as hereinbefore described in relation to compositions (A). In particular they will preferably also include an anti-oxidant, e.g. any of the specific anti-oxidants hereinbefore described in relation to compositions (A).

Of particular interest in accordance with the present invention are:

D) Compositions as defined under (C) additionally comprising: (5) a fatty acid saccharide monoester.

Compositions as defined under (D) will generally comprise the cyclosporin in a carrier medium comprising components (1.1.), e.g. Glycofurol or Transcutol, and component (5). Commonly, the cyclosporin and component (5) will each be present in compositions in accordance with (D) in molecular dispersion or solution including, where appropriate, solid solution. Component (5) will generally act in compositions in accordance with (D) as solubilizor for the cyclosporin. Compositions in accordance with (D) have the particular advantage of meeting stability and related difficulties otherwise associated with components (5) resulting from their inherent strongly hygroscopic properties.

Preferred components (5) for use in compositions in accordance with (D) are water soluble fatty acid saccharide monoesters, e.g. fatty acid monoesters of saccharides having a solubility in water of at least 3.3% at ambient temperature, e.g. at ca. 20° C., i.e. which are soluble in water at ambient temperature in an amount of at least lg monoester per 30 ml water.

The fatty acid moiety of components (5) may comprise saturated or unsaturated fatty acids or mixtures thereof. Particularly suitable components (5) are $C_{6-8}$-fatty acid saccharide monoesters, in particular water soluble $C_{6-18}$-fatty acid saccharide monoesters. Especially suitable components (5) are caproic ($C_6$), caprylic ($C_8$), capric ($C_{10}$), lauric ($C_{12}$), myristic ($C_{14}$), palmitic ($C_{16}$), oleic ($C_{18}$), ricinoleic ($C_{18}$) and 12-hydroxystearic ($C_{18}$) acid saccharide monoesters, especially lauric acid saccharide monoesters.

The saccharide moiety of component (5) may comprise any appropriate sugar residue, e.g. mono-, di- or tri-saccharide residue. Suitably, the saccharide moiety will comprise a di- or tri-saccharide residue. Preferred components (5) comprise $C_{6-14}$-fatty acid di-saccharide monoesters and $C_{1-18}$-fatty acid tri-saccharide monoesters. Especially suitable saccharide moieties are saccharose and raffinose residues.

Particularly suitable components (5) are thus: saccharose monocaproate, saccharose monolaurate, saccharose monomyristate, saccharose monooleate, saccharose monoricinoleate, raffinose monocaproate, raffinose monolaurate, raffinose monomyristate, raffinose monopalmitate and raffinose monooleate. Most preferred components (5) are raffinose monolaurate and, especially, saccharose monolaurate.

Components (5) will suitably have a hydrophilic-lipophilic balance (HLB) of at least 10.

Components (5) suitably have an ester residue purity of at least 80%, more preferably at least 90%, most preferably at least 95%. Components (5) suitably have a melting point of from about 15° to about 60° C., more preferably from about 25° to about 50° C.

Compositions in accordance with (D) may also contain further ingredients, e.g. as hereinbefore described in relation to compositions (C).

In particular, they may include a component capable of modifying the release characteristics of the composition with respect to the cyclosporin, for example thickening agents, e.g. such as hereinbefore described under (4.1.) to (4.5.).

Compositions in accordance with (D) will in particular also suitably comprise one or more anti-oxidants, e.g. as hereinbefore specified in relation to compositions (A).

Compositions in accordance with (D) will also suitably comprise one or more stabilizers or buffering agents, in particular to prevent hydrolysis of component (5) during processing or on storage. Such stabilizers may include acid stabilizors such as citric acid, acetic acid, tartaric acid or fumaric acid as well as basic stabilizers such as potassium hydrogen phosphate.

Such stabilizers or buffer agents will appropriately be added in an amount sufficient to achieve or maintain a pH within the range of from about 3 to 8, more preferably about 5 to 6, compositions in accordance with (D) having a pH within the above indicated ranges being generally preferred.

Compositions in accordance with (D) will in particular also preferably comprise a polyoxyalkylene-free hydrophilic surfactant, such as set forth under (3.1.6.) or (3.1.7.) above.

Compositions in accordance with the present invention may be employed for administration in any appropriate manner, e.g. orally, e.g. in unit dosage form, for example in hard or soft gelatin encapsulated form, parenterally or topically e.g. for application to the skin, for example in the form of a cream, paste, lotion, gel, ointment, poultice, cataplasm, plaster, dermal patch or the like, or for ophthalmic application, for example in the form of an eye-drop, -lotion or -gel formulation. Readily flowable forms, for example solutions and microemulsions, may also be employed e.g. for intralesional injection for the treatment of psoriasis, or may be administered rectally, e.g. as an enema for the treatment of inflammatory bowel disease or Crohn's disease. Compositions in accordance with the invention are however primarily intended for oral or topical application, in particular application to the skin.

The relative proportion of ingredients in the compositions of the invention will, of course, vary considerably depending on the particular type of composition concerned, e.g. whether it is a "microemulsion pre-concentrate", microemulsion, regular emulsion, solution and so forth. The relative proportions will also vary, depending on the particular function of ingredients in the composition, for example, in the case of a surfactant component of a "microemulsion pre-concentrate", on whether this is employed as a surfactant only or both a surfactant and a co-solvent. The relative proportions will also vary depending on the particular ingredients employed and the desired physical characteristics of the product composition, e.g. in the case of a composition for topical use, whether this is to be a free flowing liquid or a paste. Determination of workable proportions in any particular instance will generally be within the capability of the man skilled on the art. All indicated proportions and relative weight ranges described below are accordingly to be understood as being indicative of preferred or individually inventive teachings only and not as not limiting the invention in its broadest aspect.

The amount of cyclosporin in compositions of the invention will of course vary, e.g. depending on the intended route of administration and to what extent other components, in particular components (2) to (5) as hereinbefore described, are present. In general however the cyclosporin will be present in an amount within the range of from 0.05 especially about 0.1 to about 35% by weight based on the total weight of the composition.

Components (1) will suitably be present in the compositions of the invention in an amount of from about 0.5 to about 90% by weight based on the total weight of the composition. In the case of compositions in accordance with the invention comprising a component (1.1.) (e.g. Glycofurol or Transcutol), (1.1.) will generally be present in an amount of from about 1 to about 90% by weight, more commonly from about 5 or 10 to about 70% by weight based on the total weight of the composition. In the case of compositions in accordance with (A) or (B) above comprising a component (1.2.), (1.2.) will generally be present in an amount of from about 2 to about 50% by weight based on the total weight of the composition. In the case of compositions in accordance with the invention comprising a component (2) or (3), these will each be generally present in an amount of from about 0.5 to about 90% by weight based on the total weight of the composition. In an especially preferred aspect the present invention relates to:

E) Compositions as defined under (A) or (C) above for oral administration, e.g. in a form suitable or convenient for oral administration.

For compositions as defined under (A) to (C) intended for non-topical administration and, in particular, for oral dosage forms (E):

a) The cyclosporin will generally be present in an amount of from about 1 or 2 to about 30%, suitably from about 4 to about 25% by weight based on the total weight of the composition. More suitably the cyclosporin will be present in an amount of from about 5 to about 25, especially to about 20%, e.g. from about 5 to 15%. by weight based on the total weight of the composition;

b) Component (1.1) when present will generally be present in an amount of from about 15 to about 85, suitably from about 20 to about 80, more suitably from about 25 to about 70, e.g. from about 30 to about 50 or 60% by weight based on the total weight of the composition;

c) Cyclosporin and component (1.1.) when present will generally be present in a ratio of about 1:0.75 to 20, suitably about 1:1 to 15, more suitably about 1:1 to 5, e.g. about 1:1 or 1:1.5 to 4 p.p.w. [Cyclosporin: (1.1.)];

d) Component (1.2.) when present will generally be present in an amount of from about 3 to about 45, suitably about 5 to about 30% by weight based on the total weight of the composition;

e) Cyclosporin and component (1.2.) when present will generally be present in a ratio of about 1:0.1 to 20, suitably about 1:0.2 to 10 p.p.w. More suitably they will be present in a ratio of about 1:0.3 to 6, e.g. about 1:0.5 to 3 p.p.w. [Cyclosporin: (1.1)].

f) Component (2) when present will generally be present in an amount up to about 45%, suitably up to about 40% by weight based on the total weight of the composition. More suitably component (2) will be present in an amount of from about 2 to about 45, yet more suitably from about 3 to about 35, most suitably from about 5 or 10 to about 30% by weight based on the total weight of the composition.

g) Components (2) and (1.1) when present will generally be present in a ratio of about 1:0.5 to 40, suitably about 1:0.5 to 20, more suitably about 1:0.75 to 10, e.g. about 1:0.75 to 4 p.p.w. [(2):(1)].

h) Components (2) and (1.2) when present will suitably be present in a ratio of about 1:0.075 to 22, suitably about 1:0.1 to 15, most suitably about 1:0.15 to 6 p.p.w., e.g. about 1:0.5 to 3 p.p.w. [(2):(1.2)].

i) Components (3) when present [including both components of type (3.1.) and (3.2.)], will generally be present in an amount of up to about 90, e.g. from about 20 to about 90% by weight based on the total weight of the composition. More suitably components (3) will be present in an amount of from about 20 or 25 to about 80 or 90% by weight based on the total weight of the composition, e.g. from about 25 to about 55% when a component (1.1) is employed or from about 40 to 75% when a component (1.2) is employed.

j) Cyclosporin and component (3) [including both components of type (3.1.) and (3.2.)] when present will generally be present in a ratio of about 1:0.5 to 20, more suitably to 12 p.p.w.

Appropriately they will be present in a ratio of about 1:1 to 10 p.p.w., e.g. about 1:1 to 5 p.p.w. when a component (1.1) is present or about 1:3 to 8 p.p.w. when a component (1.2) is present. [Cyclosporin: (3)].

For compositions as defined under (A) and (B) ["microemulsion pre-concentrates" and microemulsions] the relative proportions of ingredients comprising (1) the hydrophilic phase, (2) the lipophilic phase and (3) the surfactant will vary with the concentration of cyclosporin present. They will also vary in relative proportion to each other.

Compositions according to (A) may thus be defined as comprising a cyclosporin together with (1) a hydrophilic phase [e.g. as defined under (1.1) or (1.2) above], (2) a lipophilic phase [e.g. as defined under (2.1) or (2.2) above] and a surfactant [e.g. as defined under (3.1) or (3.2) above], the relative proportions of cyclosporin: (1):(2):(3) being such that on contact with water, e.g. as hereinbefore indicated in relative proportions of 1:1 p.p.w. [cyclosporin+(1)+(2)+(3)):H$_2$O] or more, a microemulsion [e.g. of o/w type] is obtainable.

Similarly compositions according to (B) may be defined as comprising a cyclosporin together with components (1), (2) and (3) as aforesaid and water in relative proportions, e.g. as hereinbefore indicated, required to provide a microemulsion [e.g. of o/w type].

Compositions in accordance with (A) and (B) preferably comprise from about 2 to about 30, more preferably from about 5 to about 20, most preferably from about 10 to about 15% by weight of cyclosporin based on the total weight of cyclosporin plus components (1)+(2)+(3).

When (1) of compositions (A) or (B) is as defined under (1.1) above, e.g. comprises Transcutol or Glycofurol, components (1.1), (2) and (3) will preferably be present in amounts of from about 15 to about 85%, more preferably from about 25 to about 65%. of (1.1), from about 2 to about 40, more preferably from about 3 to about 35 most preferably from about 3 to about 30% of (2) and from about 15 to about 85, more preferably from about 25 to about 55 or 60% of (3), all %ages being by weight based on the total of (1.1)+(2)+(3). Use of Glycofurol is of particular interest.

When (1) of compositions (A) or (B) is 1,2-propylene glycol a(b.2) above), components (1.2.), (2) and (3) will suitably be present in amounts of from about 3 to about 35%, more preferably from about 3 to about 25% of (1.2), from about 2 to about 35%, more preferably from about 3 to about 30% of (2) and from about 45 to about 90%, more preferably from about 50 to about 90%, e.g. from about 55 to about 80% of (3), all %ages being by weight based on the total of (1.2)+(2)+(3). As previously indicated, when (1) is 1,2-propylene glycol component (3) will generally comprise both a surfactant and a co-surfactant. When a co-surfactant is employed, surfactant and co-surfactant will suitably be present in a ratio of up to about 50:1, preferably up to 20:1, more preferably up to 15:1, e.g. from 2 to 15:1 p.p.w. (surfactant: co-surfactant).

Fig. I attached, represents a three-way plot for relative concentrations of components (1.1) (e.g. Glycofurol), (2) (e.g. Miglyol 812), and (3) (e.g. Cremophore RH40) in compositions according to (A) and comprising ca. 105 cyclosporin (e.g. Ciclosporin) by weight. Relative concentration of component (1.1) increases from 0% along the left hand margin of the plot to 100% at the lower right corner, as indicated by the arrow 1.1". Concentration of component (2) increases from 0%. at the right hand margin of the plot to 100% at the loser left corner, as indicated by the arrow "2". Thus a composition comprising 50% of (1.1) and 50% of (2) only, is designated at the mid-point of the base-line of the plot. Relative concentration of component (3) increases from 0% at the base-line of the plot to 100% at the apex, as indicated by the arrow "3". Lines within the plot represent increments of 10%, from 0% at each margin to 100% at the apex opposite.

For compositions as defined under (A) and (B) the relative proportion of components (1.1), (2) and (3) will suitably lie within the area A defined by the line a of Fig. I. More suitably the relative proportion of components (1.1), (2) and (3) will lie within the area B defined by the line b of Fig. I, microemulsions based on these proportions being found to have greatest stability, e.g. of >24 hrs./an average particle size of less than 1,000 Å. Compositions in accordance with the invention comprising the components (1.1), (2) and (3) in relative proportion as defined above with reference to Fig. I accordingly represent especially preferred embodiments.

Fig. II attached, represents a three-way plot for relative concentrations of components (1.2), (2) e.g. Miglyol 812 and (3) in compositions according to (A) and comprising ca. 10% cyclosporin (e.g. Ciclosporin) by weight. In this case (3) comprises an appropriate surfactant/co-surfactant mixture, e.g. in a ratio of 11:1 p.p.w., for example comprising 11 p.p.w. Cremophor RH40 and 1 p.p.w. Glycerinmonooleate. Relative amounts of components (1.2), (2) and (3) are indicated, as for Fig. I, by arrows "1.2", "2" and "3" respectively.

For compositions as defined under (A) and (B) the relative proportions of components (1.2), (2) and (3) will suitably lie within the area X defined by the line x of Fig. II. More suitably the relative proportion of components (1.2), (2) and (3) will lie within the area Y defined by line y of Fig. II. Most suitably the relative proportion of components (1.2), (2) and (3) will lie within the area Z of Fig. I defined by line z, microemulsions based on proportions within the areas Y and Z having an average particle size of the order of 1,100 Å and <200 Å respectively and a stability, e.g. of >24 hrs.

Compositions in accordance with (E) above may additionally include a thickening agent, though, as previously indicated, this will generally be less preferred. Suitable thickening agents include any of those hereinbefore described under (4) above. The amount of thickening agent present may vary e.g. depending on the required consistency of the end product, e.g. whether it is to be in a thickened flowable form, for example for filling into a capsule or the like, or sufficiently resilient to be mouldable or formable, e.g. for use in the manufacture of tablets or the like. The amount will of course also depend on the nature of the thickening agent chosen. In general components (4), when present will be present in an amount of up to about 25% by weight based on the total weight of the composition, more suitably in an amount of up to about 15 or 20% by weight, e.g. in an amount of from 0.5 or 5 up to 15 or 20% by weight based on the total weight of the composition.

Compositions in accordance with (E) may also include further additives or ingredients, e.g. as hereinbefore described with reference to compositions (A) and (C). In particular they may comprise antioxidants, e.g. in an amount of up to about 0.5 or 1% by weight based on the total weight of the composition, and sweetening or flavouring agents, e.g. in an amount of up to about 2.5 or 5% by weight based on the total weight of the composition.

Compositions (E) in accordance with definition (A) have been found to exhibit especially advantageous properties when administered orally, e.g. in terms of both the consistancy and high level of bioavailability achieved. In particular, and in contrast with other galenic systems, e.g. as known from the art, it has been found that such compositions are compatible with tenside materials, e.g bile salts, present in the gastrointestinal tract. That is, they are fully dispersible in aqueous systems comprising such natural tensides and are thus capable of providing microemulsion systems in situ which are stable and do not exhibit precipitation or other disruption of fine particulate structure. Function of such systems on oral administration remains independent of and/or unimpaired by the relative presence or absence of bile salts at any particular time or for any given individual. Such compositions accordingly represent an especially preferred embodiment of the invention.

Compositions in accordance with (E) above will preferably be compounded in unit dosage form, e.g. by filling into orally administerable capsule shells, e.g. soft or hard gelatine capsule shells or by tabletting or other moulding process. Where compositions (E) are in unit dosage form, each unit dosage wall suitably contain between about 5 or 10 and about 200 mg cyclosporin, more suitably between about 15 or 25 and about 150 mg, e.g. 25, 50 or 100 mg cyclosporin. Thus unit dosage Norms in accordance with the invention, suitable for administration 1×, 2× or 3× up to 5× daily (e.g. depending on the particular purpose of therapy, the phase of therapy etc . . . ) will appropriately comprise e.g. about 50 mg or about 100 mg cyclosporin per unit dosage.

Compositions in accordance with (B) above for oral administration may be prepared, by addition of compositions as described in relation to (A) or (E) above to water or any other aqueous system, e.g. in relative proportions (composition:$H_2O$) as hereinbefore indicated, for example a sweetened or flavoured preparation for drinking. Such compositions may thus comprise any system as hereinabove defined or described in relation to compositions (A) or (E), plus sufficient water to form a microemulsion.

Compositions as defined under (D) above are, in particular, intended for oral administration, though use in form suitable, e.g. for topical, including dermal and topical ophthalmic, parenteral or rectal administration, as well as for intralesional injection, is also embraced.

In the case of compositions as defined under (D) the cyclosporin and required component (1.1) may be present in a ratio of about 1:0.5 to 200, preferably about 1:0.5 to 100, more preferably about 1:0.5 to 50 p.p.w. Yet more suitably they will be present in a ratio of about 1:1 to 10, more preferably 1:1 to 5, most preferably about 1:1.5 to 2.5, e.g. about 1:1.6 or 1:2 p.p.w. (Cyclosporin: (1.1)1. Cyclosporin and required component (5) will suitably present in a ratio of about 1:3 to 200, preferably about 1:3 to 100, more preferably about 1:3 to 50 p.p.w. Yet more suitably they will be present in a ratio of about 1:5 to 20, preferably about 1:5 to to 10, most preferably about 1:6.0 to 6.5, e.g. about 1:6.25 p.p.w. [Cyclosporin:(1.1)].

Suitably compositions in accordance with (D) will be made up in unit dosage form, whether for oral administration or otherwise.

The amount of cyclosporin present in such unit dosage forms will of course vary depending on e.g. the condition to be treated, the intended mode of administration and the effect desired. In general however, unit dosage forms in accordance with (D) will suitably comprise from about 2 to about 200 mg cyclosporin, per unit dosage.

Suitable dosage forms for oral administration include e.g. liquids, granulates and the like. Preferred dosage forms are however unit dosage forms, for example tabletted or encapsulated forms, in particular hard or soft gelatin encapsulated forms.

Unit dosage forms for oral administration in accordance with (D) will suitably comprise from about 5 or 10 to about 200 mg, more suitably from about 15 or 20 to about 100 mg, e.g. 25, 50 or 100 mg cyclosporin per unit dosage.

Compositions (D) have the further advantage that they are able to provide the basis for compositions exhibiting modified release characteristics, for example delayed release of cyclosporin or release of cyclosporin over prolonged periods of time, e.g. following oral administration. Such compositions additionally comprise a component capable of modifying the release characteristics of the composition with respect to the cyclosporin. Such components include, for example, (4), a thickening agent, e.g. in accordance with any of (4.1) to (4.5) above.

When compositions (D) comprise a component (4), this is suitably present in an amount of from about 0.5 to 50%, more preferably from about 1 to 20%, most preferably from about 2 to 10% by weight based on the total weight of Cyclosporin plus (1.1)+(4)+(5).

As previously indicated, compositions in accordance with (D) will advantageously include one or more stabilizers or buffering agents or polyoxyalkylene-free surfactants. Such stabilizors and/or buffering agents will suitably be present in an amount of up to 5% by weight or, when citric or acetic acid are employed, up to 10% by weight based on the weight of cyclosporin plus (1.1)+(5). When a surfactant as aforesaid is present, this is suitably present in an amount of from about 5 to about 50, more preferably from about 10 to about 25% by weight based on the weight of component (5).

Compositions in accordance with (D) will also suitably comprise further additives in particular flavouring agents or, in particular, anti-oxidants. Suitable anti-oxidants and quantities employed are as hereinbefore described in relation to compositions (E).

Compositions in accordance with (D) will also preferably be free or substantially free of lower alkanols, in particular ethanol, e.g. comprise less than 5%, more preferably less then 2%, e.g. from 0 to 1%, lower alkanolic components based on the total weight of the composition.

Compositions as defined under (A) to (C) are also of particular interest for topical administration. Accordingly in a yet further aspect the present invention provides:

F) Compositions as defined under any one of (A) to (C) above for topical, especially for dermal application, i.e. in a form suitable or convenient for topical application.

Where topical administration is contemplated, the cyclosporln will suitably be present in an amount of from about 0.05, more preferably from about 0.1, to about 15% by weight based on the total weight of the composition. More preferably the cyclosporin will be present in an amount of from about 0.1 to about 10% by weight.

In the case of compsitions (F) which are compositions in accordance with (A) or (B), the relative proportion of components (1), (2) and (3) will be as hereinbefore described for such compositions, e.g. with reference to Figs. I and II.

Compositions (F) in accordance with (C) the other hand may take any suitable form, e.g. comprise solutions, suspensions, dispersions and regular emulsions. Component (1.1) may suitably be present in such compositions in an amount of from about 1 to about 70%, preferably from about 5 to about 50%, more preferably from about 7 to about 25% by weight based on the total weight of the composition.

Compositions (F) will suitably comprise one or more carriers or diluents and/or other ingredients providing a carrier system, e.g. thickening agents, emulsifying agents, preserving agents, moisturising agents, colourants and so forth.

Compositions (F) may be in any form suitable for topical application, e.g. application to the skin surface, for example flowable, e.g. liquid or semi-liquid form, in the form of a powder or in the form of a topically applicable spray. Examples of suitable flowable forms include e.g. gels, including oil-in-water and water-in-oil emulsions or microemulsions, creams, pastes amd ointments and the like as well as lotions, and tinctures, etc. Such compositions also include, e.g. cataplasms and poultices as well as transdermal patch systems.

Selection of excipients for the preparation of such formulations will, of course, be determined by the type of formulation desired as well as the particular condition to be treated, the status of the condition, area to be treated, skin condition and effect desired. Thus chronic psoriatic plaques will more suitably be treated with hydrophobic, e.g. fatbased compositions, for example compositions in accordance with the invention comprising a petrolatum based ointment or cream as carrier medium. In contrast, compositions for use in the treatment of disease conditions involving acute phase inflammatory processes will more appropriately be treated with more hydrophilic compositions, e.g. compositions in accordance with the invention in the form of an oil-in-water emulsion or gel. Although, compositions (F) may comprise, e.g. lower alkanols, for example ethanol, for example as diluent or diluent component, use of these will preferably be avoided, e.g. where compromised skin is to be treated, as in the case of psoriasis. Preferred compositions (F) are thus free or substantially alkanol free, e.g. contain less than 5%, more preferably less than 2%, e.g. from about 0 to 1% by weight alkanolic components, in particular of ethanol.

Especially preferred compositions (F) are compositions in accordance with (A), (B) or (C) additionally comprising: (6) a (further) pharmaceutically acceptable diluent or carrier which is non-miscible with component (1.1.). Compositions as aforesaid will preferably take the form of a water-free or substantially water-free emulsion, i.e. comprise less than 10%, preferably less than 5%, most preferably less than 1% water. Such emulsions include both emulsions comprising component (1.1.) in (6), and emulsions comprising (6) in (1.1.). Preferably they will comprise an emulsion of (1.1.) in (6).

Suitable components (6) include, for example:

6.1. Solid hydrocarbons, for example petroleum jellies, e.g. white petrolatum or Vaseline$^R$, ceresin and solid paraffins, as well as waxes including animal, vegetable and synthetic waxes such as, for example, spermaceti, carnauba and bees wax;

6.2. Liquid hydrocarbons, e.g. liquid paraffins and fatty acid esters such as isopropylmyristate and cetyl palmitate;

6.3. Non-volatile silicones including silicone oils and pastes, and silicone-polyalkyleneoxide co-polylymers [c.f. Fiedler, loc.cit., pp. 1109 and 1110] for example such as known and commercially available under the trade name Piroethicon.

Components (6) will suitably be present in compositions (F) in an amount of up to about 80%, e.g. from about 5 to about 70%, preferably from about 25 to about 60% by weight based on the total weight of the composition.

By use of individual ingredients (6) or mixtures thereof, emulsions may be obtained in liquid or semi-solid form depending on, e.g., desired requirements for topical application.

Compositions (F) will suitably also comprise a surfactant. Suitable surfactants include, in particular, lipophilic surfactants, including any of those listed under (3.2.1.) to (3.2.7.) above, especially surfactants having an HLB of ca. 5–7. Examples of surfactants of particular utility in relation to compositions (F) include for example, surfactants as described under (3.1.2.), and (3.2.3.) above as well as glycerol monstearate, propyleneglycol monostearate, diethyleneglycol monostearate and glycerol ricinoleate.

Surfactants as aforesaid will suitably be present in compositions (F) in an amount of up to about 60%, e.g. from about 2 to about 50%, preferably from about 10 to about 40% by weight based on the total weight of the composition.

Compositions (F) may further comprise one or more consistency promoting agents, for example microcrystalline waxes, vegetable oils such as olive oils, corn oils and kernel oils, and vegetable oil derivatives including hydrogenated vegetable oils and vegetable oil partial-glycerides, e.g. in an amount of from about 0.1 to about 10%, preferably from about 1 to about 5% weight based on the total weight of the composition.

Compositions (F) will also suitably comprise:

an anti-oxidant, e.g. any of the antioxidants hereinbefore described in relation to compositions (A), for example in an amount of from about 0.01 to about 0.5% by weight based on the total weight of the composition;

an anti-bacterial agent, e.g. benzyl alcohol, methyl- or propyl-paraben, benzalkonium chloride, benzoic acid, sorbic acid or chlorobutanol, for example in an amount of from about 0.05 to about 2% by weight based on the total weight of the composition;

a stabilizer such as microcrystalline starch, sodium EDTA or magnesium sulfate, e.g. in an amount of from about 0.1 to about 10% by weight based on the total weight of the composition; and/or a skin penetration enhancer, for example a $C_{12-24}$ mono- or poly-unsaturated fatty acid or alcohol (e.g. vaccenic, cis-vaccenic, linoleic, linolenic, elaidic oleic, petroselinic, erucic or nervonic acid or any of their corresponding alcohols, especially oleic acid or oleyl alcohol), or 1-dodecylazacycloheptan-2-one also known as Azone (c.f. Fiedler, loc. cit., p. 190), e.g. in an amount of from about 1 to about 20, suitably from about 3 to about 15% by weight based on the total weight of the composition.

In addition to the foregoing the present invention also provides a process for the production of a pharmaceutical composition as hereinbefore defined, e.g. as hereinbefore defined under anyone of (A) to (F) above, which process comprises bringing the individual components thereof into intimate admixture and, when required compounding the obtained composition in unit dosage form, for example filling said composition into gelatin, e.g. soft or hard gelatin, capsules.

In a more particular embodiment the invention provides a process for the preparation of a composition as defined under any one of (A) to (D) above, which process comprises bringing a cyclosporin, e.g. Ciclosporin, into inimite admixture with a component (1.1) as hereinbefore defined to obtain a composition as defined under (C) and, optionally, a component (5) as hereinbefore defined to obtain a composition as defined under (D), or with a component (1.2) as hereinbefore defined, whereby optionally when a component (1.1) is employed, or necessarily when a component (1.2) is employed, said aforesaid ingredients are further combined with a component (2) and a component (3) as hereinbefore defined, the relative proportions of component (1.1) or (1.2), (2) and (3) being chosen such that a composition as defined under (A) is obtained and further, when required, contacting said obtained composition (A) with water, so as to obtain a composition as defined under (B) and when required, compounding an obtained composition (A), (C) or (D) in unit dosage form, e.g. soft or hard gelatin capsule form.

In a specific embodiment the present invention provides a process for producing a composition as defined under (A) above, which process comprises intimately admixing a cyclosporin, e.g Ciclosporin, with a component (1.1) or (1.2) as hereinbefore defined, and a component (2) and a component (3) as hereinbefore defined, the relative proportion of the components (1.1) or (1.2), (2) and (3) being selected relative to the quantity of cyclosporin employed such that a "microemulsion pre-concentrate", e.g. composition capable on addition to water, e.g. in a ratio of at least 1:1 p.p.w. (composition:$H_2O$) of providing a system comprising a dispersed or particle phase of which the individual particles have a size of less than 2,000 Å, preferably of from about 100 to about 1,000 Å is obtained.

The preferred cyclosporin in relation to the compositions of the invention is Ciclosporin. A further preferred cyclosporin to which the teachings of the present invention are applicable is $[Nva]^2$-Ciclosporin, also known as cyclosporin G.

Figure 1:
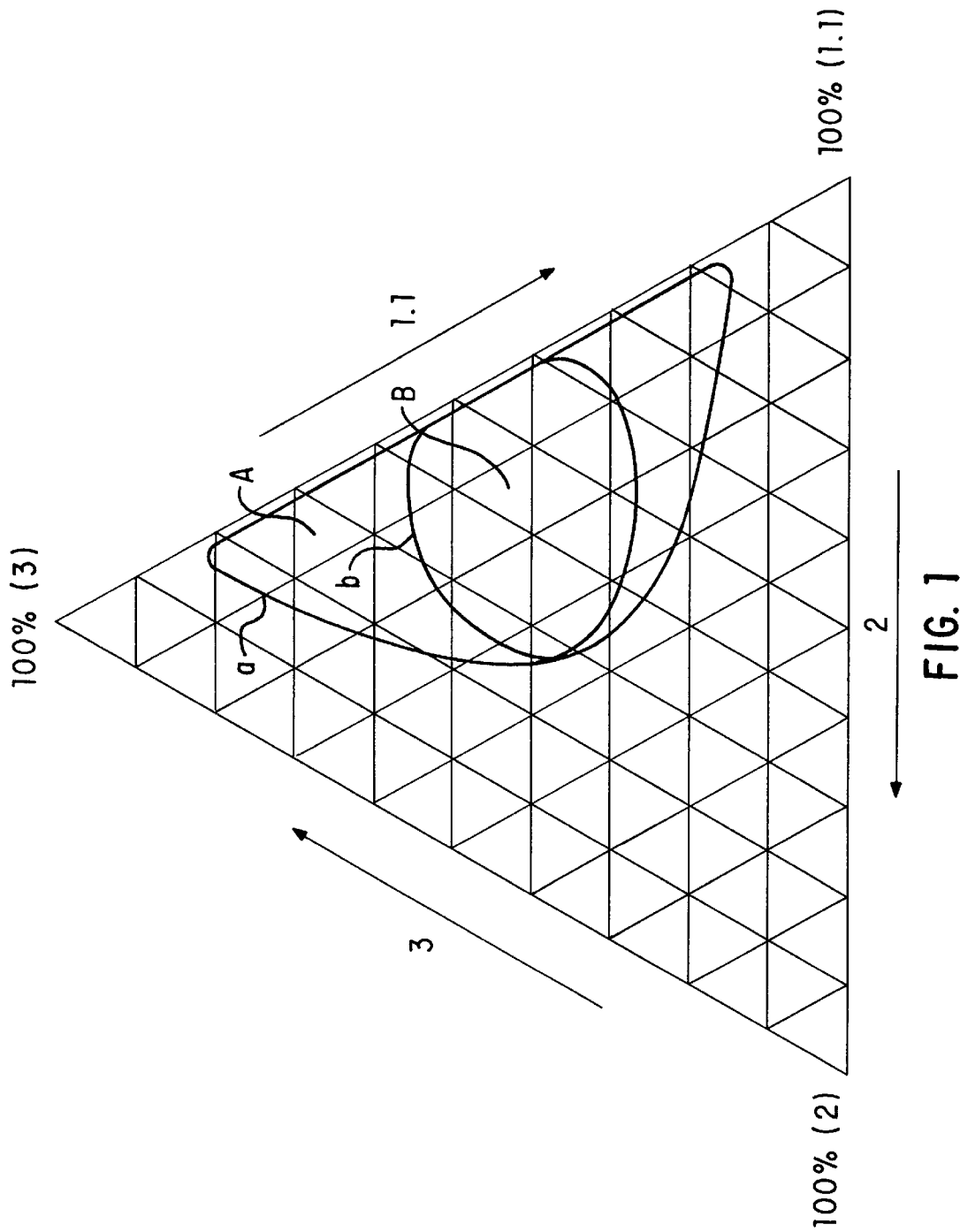
FIG. 1 represents a three-way plot for relative concentrations of components (1. 1) (e.g. GLYCOFUROL), (2) (e.g. MIGLYOL 812), and (3) (e.g. CREMOPHORE RH40) in compositions according to (A) and comprising ca. 10% cyclosporin by weight, Relative concentration of component (1.1) increases from 0% along the left hand margin of the plot to 100% at the lower right corner, as indicated by the arrow "1.1". Concentration of component (2) increases from 0% at the right hand margin of the plot to 100% at the lower left corner, as indicated by the arrow "2". Relative concentration of component (3) increases from 0% at the baseline of the plot to 100% at the apex, as indicated by the arrow "3". Lines within the plot represent increments of 10%, from 0% at each margin to 100% at the apex opposite. The relative proportion of components (1.1), (2) and (3) will suitably lie within the area A defined by the line a of FIG. 1. More suitably, the relative proportion of components (1.1), (2), and (3) will lie within the area B defined by the line b of FIG. 1.
Figure 2:
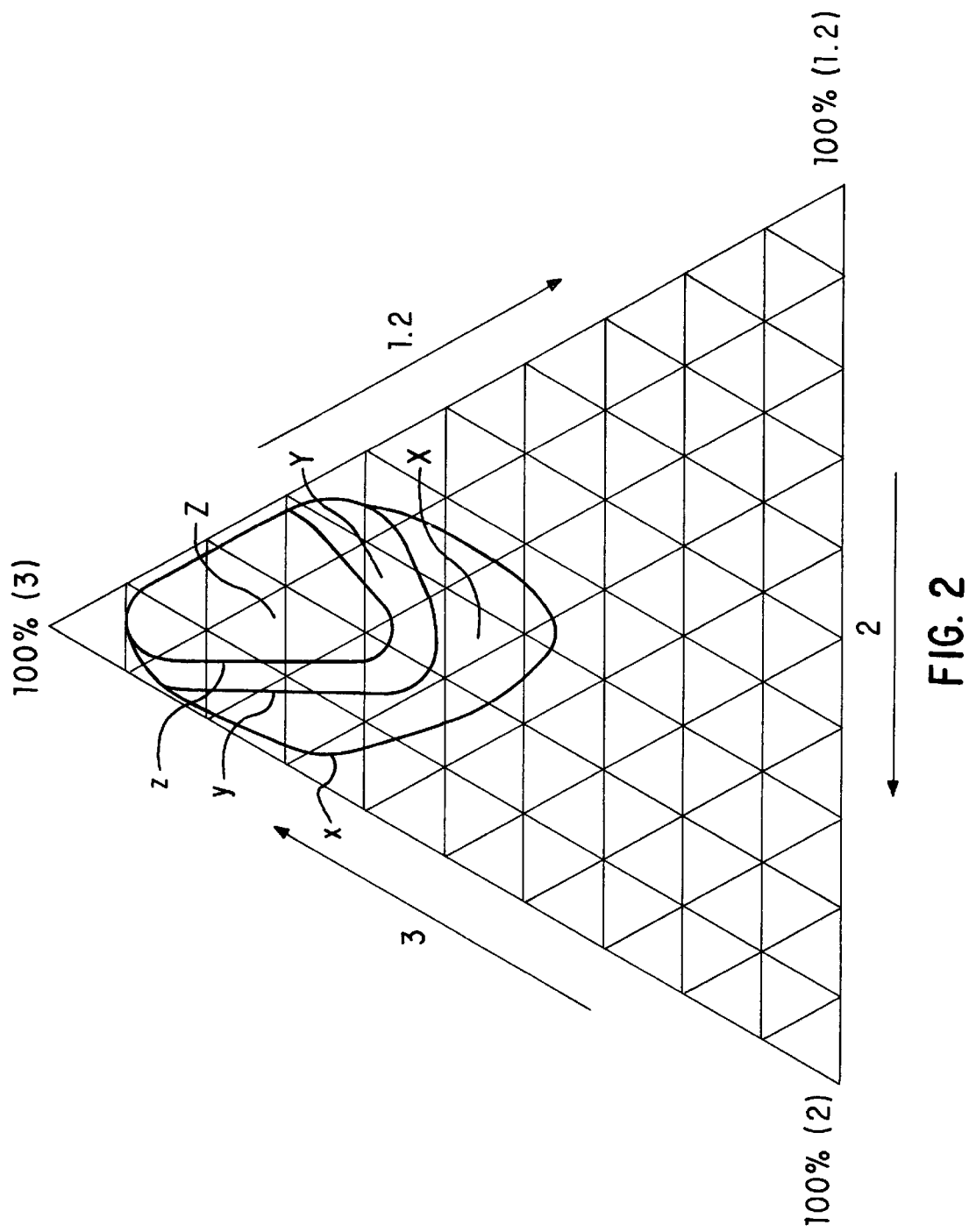
FIG. 2 represents a three-way plot for relative concentrations of components (1.2), (2) e.g. MIGLYOL 812 and (3) in compositions according to (A) and comprising ca. 10% cyclosporin by weight. In this case (3) comprises an appropriate surfactant/co-surfactant mixture, e.g. in a ratio of 11.1 parts by weight (pbw), for example comprising 11 pbw CREMOPHORE RH40 and 1 pbw Glycerinmonooleate. Relative amounts of components (1.2), (2) and (3) are indicated, as for FIG. 1, by arrows "1.2", "2" and "3" respectively. The relative proportions of components (1.2), (2) and (3) will suitably lie within the area X defined by line x of FIG. 2; more suitably within the area Y defined by line y of FIG. 2; and most suitably within the area Z of FIG. 2 defined by line z.
Figure 3:
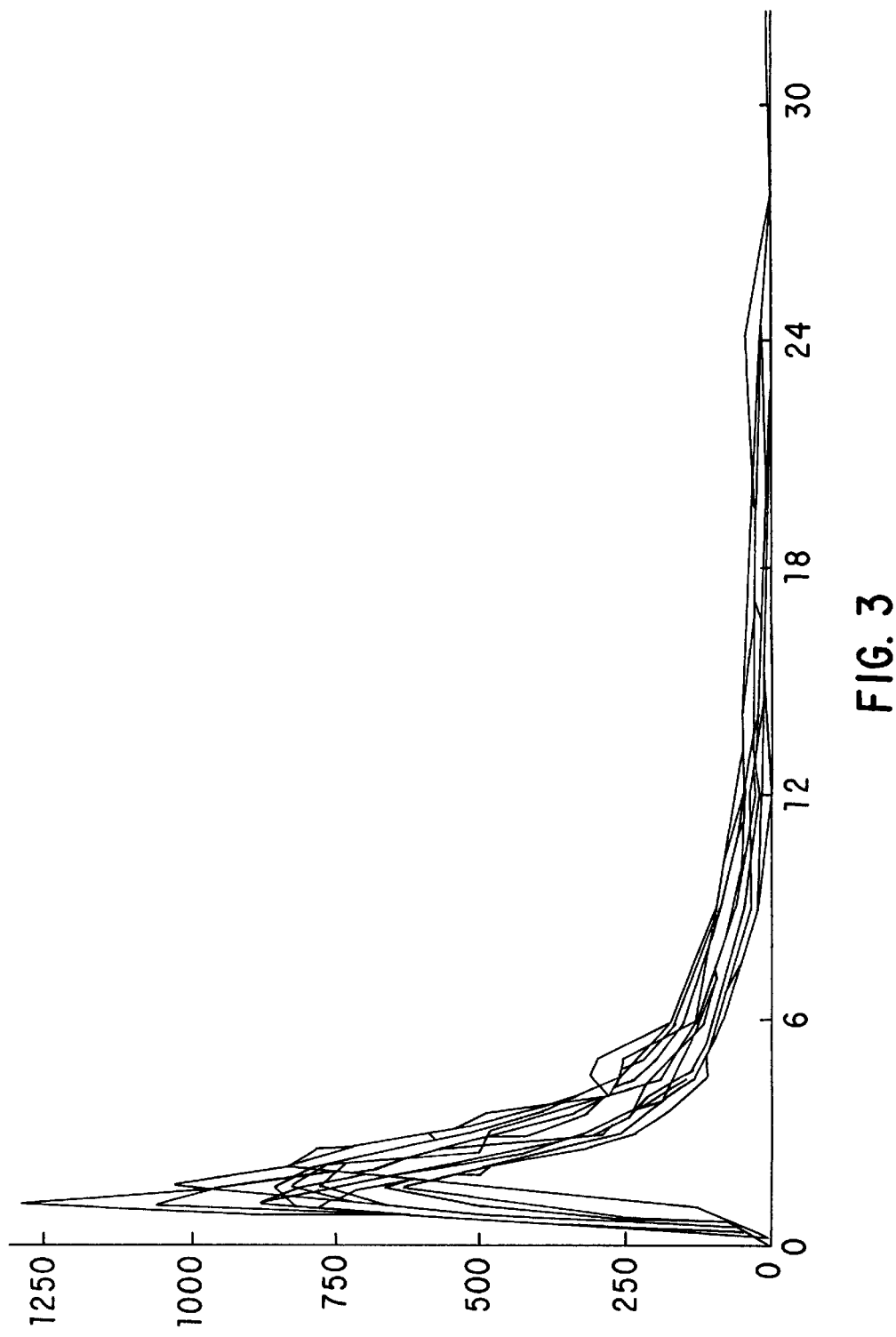
FIGS. 3 and 4 provide superimposed graphical representations from a trial of whole blood Ciclosporin concentrations recorded for 12 trial participants following single oral administrations of COMPOSITION I (FIG. 3) and COMPOSITION X (FIG. 4), each in an amount providing a Ciclosporin dosage of 150 mg, as determined by specific monoclonal RIA. Blood concentration (in ng/ml) is recorded vertically, and time (in hrs.) horizontally.
Figure 4:
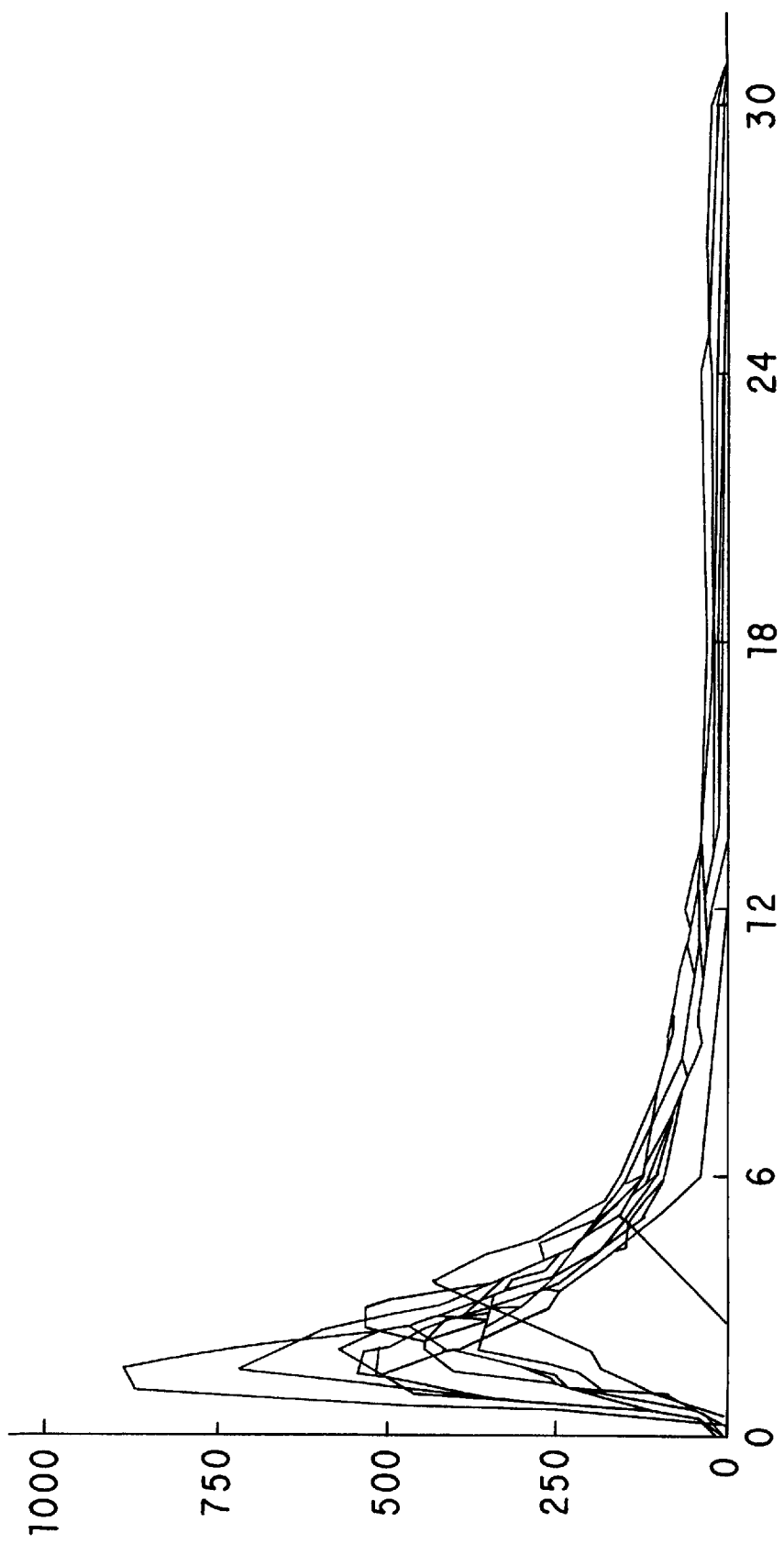

The following examples are illustrative of compositions in accordance with the present invention. Examples 1,2,4,5 and 7 illustrate the preparation of compositions in oral unit dosage form, suitable for use, e.g. in the prevention of transplant rejection or for the treatment of autoimmune disease, e.g. any of the autoimmune diseases or conditions hereinbefore described, on administration of from 1 to 5 unit dosages/day. Examples 3 and 6 illustrate the preparation of compositions for topical application, suitable for treatment, e.g. of atopic or contact dermatitis, psoriasis or hair loss, on application at the desired site of therapy, e.g. dermatitidic reaction or psoriatic lesion or to the scalp, at regular intervals, e.g. once, twice or three times per day.

The examples are described with particular reference to Ciclosporin. However, equivalent compositions may be obtained employing any other appropriate cyclosporin. In particular equivalent compositions may in all cases be obtained on replacement of Ciclosporin with [Nva]$^2$-Ciclosporin in the same amount as indicated for Ciclosporin.

EXAMPLE 1

Preparation of oral dosage forms: "microemulsion pre-concentrate" type:

| 1.1. | COMPONENT | | QUANTITY (mg/capsule) |
|---|---|---|---|
| | (1.1) | Cyclosporin (e.g. Ciclosporin) | 50.0 |
| | (1.1) | Glycofurol 75 | 180.0 |
| | (2.1) | Miglyol 812 | 90.0 |
| | (3.1.1) | Cremophor RH 40 | 180.0 |
| | | TOTAL | 500.0 |

The cyclosporin is dissolved in (1.1) with stirring at room temperature and (2.1) and (3.1.1) are added to the obtained solution, again with stirring. The obtained mixture is filled into a size 1 hard gelatin capsule and sealed using Quali-Seal technique.

The following compositions may be prepared analogously for filling into size 1 or 2 hard gelatin capsules:

| 1.2. | COMPONENT | | QUANTITY (mg/capsule) |
|---|---|---|---|
| | (1.1) | Cyclosporin (e.g. Ciclosporin) | 50.0 |
| | (1.1) | Glycofurol 75 | 180.0 |
| | (2.1) | Miglyol 812 | 78.0 |
| | (3.1.1) | Cremophor RH 40 | 192.0 |
| | | TOTAL | 500.0 |

| 1.3. | COMPONENT | | QUANTITY (mg/capsule) |
|---|---|---|---|
| | (1.1) | Cyclosporin (e.g. Ciclosporin) | 50.0 |
| | (1.1) | Glycofurol 75 | 200.0 |
| | (2.1) | Miglyol 812 | 60.0 |
| | (3.1.1) | Nikkol HCO-40 | 120.0 |
| | | Ethanol* | 19.0 |
| | | Ascorbylpalmitate** | 1.0 |
| | | TOTAL | 450.0 |

*Co-solvent (hydrophilic phase)
**Antioxidant

| 1.4. | COMPONENT | | QUANTITY (mg/capsule) |
|---|---|---|---|
| | (1) | Cyclosporin (e.g. Ciclosporin) | 50.0 |
| | (1) | Glycofurol 75 | 100.0 |
| | (2.1) | Miglyol 812 | 75.0 |
| | (3.1.7) | Lecithin | 75.0 |
| | | TOTAL | 300.0 |

| 1.5. | COMPONENT | | QUANTITY (mg/capsule) |
|---|---|---|---|
| | (1.1) | Cyclosporin (e.g. Ciclosporin) | 100.0 |
| | (1.1) | Glycofurol 75 | 260.0 |
| | (1.2) | Propyleneglycol | 50.0 |
| | (2.1) | Myritol 318 | 100.0 |
| | (3.1.1) | Cremophor RH 40 | 340.0 |
| | | BHA* | 5.0 |
| | | TOTAL | 855.0 |

*Anti-oxidant

| 1.6. | COMPONENT | | QUANTITY (mg/capsule) |
|---|---|---|---|
| | (1.2) | Cyclosporin (e.g. Ciclosporin) | 50.0 |
| | (1.2) | 1,2-Propyleneglycol | 68.0 |
| | (2.1) | Miglyol 812 | 68.0 |
| | (3.1.1) | Cremophor RH 40 | 250.0 |
| | (3.2.5) | Glycerol monooleate* | 24.0 |
| | | TOTAL | 460.0 |

| 1.7. | COMPONENT | | QUANTITY (mg/capsule) |
|---|---|---|---|
| | (1.2) | Cyclosporin (e.g. Ciclosporin) | 50.0 |
| | (1.2) | 1,2-Propyleneglycol | 68.0 |
| | (2.1) | Miglyol 812 | 24.0 |
| | (3.1.1) | Cremophor RH 40 | 250.0 |
| | (3.2.5) | Glycerol monooleate* | 68.0 |
| | | TOTAL | 460.0 |

| 1.8. | COMPONENT | | QUANTITY (mg/capsule) |
|---|---|---|---|
| | (1.2) | Cyclosporin (e.g. Ciclosporin) | 100.0 |
| | (1.2) | 1,2-Propyleneglycol | 75.0 |
| | (2.1) | Miglyol 812 | 25.0 |
| | (3.1.1) | Cremophor RH 40 | 150.0 |
| | (3.2.5) | Glycerol monooleate* | 150.0 |
| | | TOTAL | 500.0 |

| 1.9. | COMPONENT | | QUANTITY (mg/capsule) |
|---|---|---|---|
| | (1.2) | Cyclosporin (e.g. Ciclosporin) | 50.0 |
| | (1.2) | 1,2-Propyleneglycol | 200.0 |
| | (2.1) | Miglyol 812 | 50.0 |
| | (3.1.1) | Cremophor RH 40 | 150.0 |
| | (3.2.7) | Generol 122 E16* | 50.0 |
| | | TOTAL | 500.0 |

| 1.10. | COMPONENT | | QUANTITY (mg/capsule) |
|---|---|---|---|
| | (1.2) | Cyclosporin (e.g. Ciclosporin) | 50.0 |
| | (1.2) | 1,2-Propyleneglycol | 75.0 |
| | (2.1) | Miglyol 812 | 75.0 |

27
-continued

| 1.10. COMPONENT | | QUANTITY (mg/capsule) |
|---|---|---|
| (3.1.1) | Cremophor RH 40 | 250.0 |
| (3.2.7) | Generol 122 E25* | 50.0 |
| | TOTAL | 500.0 |

*Co-surfactant

Compositions 1.1, 1.2, 1.6 and 1.7 are especially preferred. Equivalent compositions to 1.1 to 1.5 can in all cases be prepared replacing the Glycofurol component with Transcutol in the same or equivalent amount.

Equivalent compositions to 1.1 to 1.5 may be prepared but replacing the 50 mg amount of cyclosporin with 15, 20 or 100 mg cyclosporin (e.g. Ciclosporin) the quantities of the remaining components for each composition remaining as indicated.

EXAMPLE 2

Preparation of oral dosage forms: thickened "microemulsion pre-concentrate" type:

| 2.1. COMPONENT | | QUANTITY (mg/capsule) |
|---|---|---|
| (1.1) | Cyclosporin (e.g. Ciclosporin) | 50.0 |
| (2.1) | Glycofurol 75 | 180.0 |
| (3.1.1) | Miglyol 812 | 90.0 |
| (4.2) | Cremophor RH 40 | 180.0 |
| | Methocel K100 | 100.0 |
| | TOTAL | 600.0 |

Ciclosporin and (1.1) to (3.1.1) are combined as in example 1 and the obtained mixture mixed homogeneously with (4.2). The product is filled into size 2 hard gelatin capsules.

The following composition may be obtained analogously:

| 2.2. COMPONENT | | QUANTITY (mg/capsule) |
|---|---|---|
| (1.1) | Cyclosporin (e.g. Ciclosporin) | 50.0 |
| (2.1) | Glycofurol 75 | 180.0 |
| (3.1.1) | Miglyol 812 | 90.0 |
| (4.6) | Cremophor RH 40 | 180.0 |
| (4.2) | Aerosil 200 | 9.0 |
| | Methocel K100 | 100.0 |
| | TOTAL | 609.0 |

| 2.3. COMPONENT | | QUANTITY (mg/capsule) |
|---|---|---|
| (1.1) | Cyclosporin (e.g. Ciclosporin) | 100.0 |
| (2.1) | Glycofurol | 210.0 |
| (3.1.1) | Myritol 318 | 90.0 |
| (4.2) | Nikkol HCO-60 | 170.0 |
| | Klucel EF | 30.0 |
| | TOTAL | 600.0 |

Equivalent compositions to 2.1 to 2.3 can be prepared replacing the Glycofurol component with Transcutol in the same or equivalent amount.

28
EXAMPLE 3

Preparation of topically applicable form: "microemulsion pre-concentrate" type:

| COMPONENT | | % BY WEIGHT |
|---|---|---|
| (1.1) | Cyclosporin (e.g. Ciclosporin) | 0.1 |
| (2.1) | Glycofurol | 50.0 |
| (3.1.1) | Miglyol 812 | 16.6 |
| | Cremophor RH 40 | 33.3 |

The above composition is prepared analogously to example 1. An equivalent composition is obtained on replacement of the Glycofurol component with Transcutol. The composition may be made the basis of a cream, gel or the like by combination with further additives, e.g. hydrocolloid thickening agents, paraffins etc . . . as hereinbefore described.

EXAMPLE 4

Preparation of oral dosage forms: regular emulsion pre-concentrate type:

| 4.1. COMPONENT | | QUANTITY (mg/capsule) |
|---|---|---|
| (1.1) | Cyclosporin (e.g. Ciclosporin) | 100.0 |
| (3.1.1) | Transcutol | 154.0 |
| (3.2.1) | Cremophor RH 40 | 146.0 |
| | Labrafil M 1944 CS | 50.0 |
| | TOTAL | 450.0 |

Cyclosporin is dissolved in (1.1) with stirring at room temperature and (3.1.1) and (3.2.1) added to the obtained solution, again with stirring. The obtained mixture is filled into size 1 hard gelatin capsules and sealed employing Quali-Seal technique.

The following compositions may be prepared analogously for filling into size 1 or 2 hard gelatin capsules as appropriate.

| 4.2. COMPONENT | | QUANTITY (mg/capsule) |
|---|---|---|
| (1.1) | Cyclosporin (e.g. Ciclosporin) | 50.0 |
| (3.1.1) | Transcutol | 80.0 |
| (3.2.1) | Cremophor RH 40 | 75.0 |
| | Labrafil M 2130 CS | 25.0 |
| | TOTAL | 230.0 |

| 4.3. COMPONENT | | QUANTITY (mg/capsule) |
|---|---|---|
| (1.1) | Cyclosporin (e.g. Ciclosporin) | 100.0 |
| (3.1.1) | Glycofurol 75 | 150.0 |
| | Nikkol HCO-40 | 200.0 |
| | TOTAL | 450.0 |

-continued

| 4.4. | COMPONENT | | QUANTITY (mg/capsule) |
|---|---|---|---|
| | (1.1) | Cyclosporin (e.g. Ciclosporin) | 50.0 |
| | (3.1.1) | Transcutol | 100.0 |
| | (3.2.1) | Cremophor RH 40 | 94.0 |
| | | Labrafil M 1944 | 31.0 |
| | | TOTAL | 275.0 |

Equivalent compositions may be prepared by replacing Transcutol in 4.1, 4.2 or 4.4 with the same or equivalent amount of Glycofurol, or the Glycofurol in 4.3 with the same or equivalent amount of Transcutol.

EXAMPLE 5

Preparation of oral dosage forms: thickened emulsion pre-concentrate type:

| 5.1. | COMPONENT | | QUANTITY (mg/capsule) |
|---|---|---|---|
| | (1.1) | Cyclosporin (e.g. Ciclosporin) | 50.0 |
| | (3.1.1) | Transcutol | 80.0 |
| | (3.2.1) | Cremophor RH 40 | 75.0 |
| | (4.1) | Labrafil M 1944 CS | 25.0 |
| | | Eudragit E | 50.0 |
| | | TOTAL | 280.0 |

(3.2.1) and (4.1) are combined with and dissolved in (1.1) with stirring and light warming. Cyclosporin is then added with light warming and further stirring and the product filled into size 2 hard-gelatin capsules and sealed.

The following compositions can be prepared analogously for filling into size 1 or 2 hard gelatin capsules as appropriate:

| 5.2. | COMPONENT | | QUANTITY (mg/capsule) |
|---|---|---|---|
| | (1.1) | Cyclosporin (e.g. Ciclosporin) | 100.0 |
| | (3.1.4) | Transcutol | 180.0 |
| | (3.1.6) | Pluronic F68 | 140.0 |
| | (4.2) | Sodium laurylsulphate | 5.0 |
| | | Sodium carboxymethylcellulose | 25.0 |
| | | TOTAL | 350.0 |

| 5.3. | COMPONENT | | QUANTITY (mg/capsule) |
|---|---|---|---|
| | (1.1) | Cyclosporin (e.g. Ciclosporin) | 50.0 |
| | (3.1.1) | Transcutol | 163.0 |
| | (3.2.1) | Cremophor RH 40 | 100.0 |
| | (4.3) | Labrafil M 1944 CS | 35.0 |
| | | Kollidon 30 | 72.0 |
| | | TOTAL | 420.0 |

Equivalent compositions may be prepared by replacing the Transcutol component with Glycofurol in the same or equivalent amount.

EXAMPLE 6

Preparation of topical dosage forms: emulsion type:

The following are prepared by intimate admixture of the indicated ingredients analogously to examples 2 and 5 above, to provide ointment preparations suitable for topical application:

| 6.1. | COMPONENT | | % BY WEIGHT |
|---|---|---|---|
| | (1.1) | Cyclosporin (e.g. Ciclosporin) | 0.1 |
| | (3.1.1) | Transcutol | 15.0 |
| | (3.2.1) | Cremophor RH 40 | 5.0 |
| | (3.2.5) | Labrafil M 213 | 15.0 |
| | (6.2) | Glycerolmonostearate | 10.0 |
| | | White petrolatum | 54.9 |

| 6.2. | COMPONENT | | % BY WEIGHT |
|---|---|---|---|
| | (1.2) | Cyclosporin (e.g. Ciclosporin) | 0.1 |
| | (3.2.5) | Glycofurol | 15.0 |
| | (6.1) | Glycerolmonostearate | 8.0 |
| | (6.1) | Mineral oil | 39.0 |
| | | White petrolatum | 37.9 |

EXAMPLE 7

Preparation of oral dosage forms: sugar ester type:

| 7.1. | INGREDIENT | | AMOUNT (mg/capsule) |
|---|---|---|---|
| | (1.1) | Cyclosporin (e.g. Ciclosporin) | 50.0 |
| | (5) | Glycofurol | 100.0 |
| | | Saccharose monolaurate L-1695* | 312.5 |
| | | TOTAL | 462.0 |

| 7.2. | INGREDIENT | | AMOUNT (mg/capsule) |
|---|---|---|---|
| | (1.1) | Cyclosporin (e.g. Ciclosporin) | 50.0 |
| | (5) | Transcutol | 80.0 |
| | | Saccharose monolaurate L-1695* | 312.5 |
| | | TOTAL | 442.5 |

| 7.3. | INGREDIENT | | AMOUNT (mg/capsule) |
|---|---|---|---|
| | (1.1) | Cyclosporin (e.g. Ciclosporin) | 50.0 |
| | (5) | Glycofurol | 100.0 |
| | (4.2) | Saccharose monolaurate L-1695* | 312.5 |
| | | Klucel LF | 50.0 |
| | | TOTAL | 512.5 |

(*Product commercially available from Mitsubishi-Kasei Food Corp., Tokyo 104, Japan: HLB-value = at least 12.3: lauryl ester residue purity = at least 95%: M.P. = ca. 35° C.: decomposition at ca. 235° C.: surface tension of 0.1% by weight aqueous solution = ca. 72.0 dyn/cm at 25° C.)

The composition of example 7.1 is prepared by dissolving cyclosporin and (5) with stirring and warming over an oil bath at 100° C. in component (1.1). The composition of examples 7.2 and 7.3 are prepared analogously.

The obtained compositions are filled, with warming, into hard gelatin capsules size 1 (compositions 7.1 and 7.2) or 0 (composition 7.3).

Utility of compositions in accordance with the invention may be shown in animal or clinical trials, for example performed as follows:

Bioavailability Study For Compositions in Accordance With the Invention in the Dog a) Test compositions

| | | |
|---|---|---|
| COMPOSITION I | as per example | 1.1 |
| COMPOSITION II | as per example | 1.2 |
| COMPOSITION III | as per example | 1.6 |
| COMPOSITION IV | as per example | 2.1 |
| COMPOSITION V | as per example | 2.2 |
| COMPOSITION VI | as per example | 4.4 |
| COMPOSITION VII | as per example | 5.3 | b) Test method

Groups of 8 beagle dogs (male, ca. 11–13 kg) are used. Animals receive no food within 18 hours of administration of test composition but are allowed free access to water until administration. Test compositions are administered by gavage, followed by 20 ml NaCl 0.9% solution. The animals are allowed free access to food and water three hours after administration of test composition.

2 ml blood samples (or 5 ml for the blank) are taken from the vena saphena and collected in 5 ml plastic tubes containing EDTA at −15 min. (blank), 30 min., and 1, 1.5, 2, 3, 4, 6, 8, 12 and 24 hours post administration. Blood samples are stored at −18° C. pending assay.

Blood samples are analysed by RIA. Areas under the blood drug concentration versus time curves are calculated by the trapezoidal rule. Analysis of variance is performed with respect to AUC (area under curve), Cmax (maximum concentation) and Tmax (time of maximum).

c) Results

Calculated average AUC (in ng hr./ml$^{-1}$) and Cmax (in ng/ml$^{-1}$) values from typical trial runs are shown in the following table, together with calculated variation in response between test animals receiving the same composition (CV).

| COMPOSITION | AUC (0–24 h) | CV (%) | Cmax | CV % |
|---|---|---|---|---|
| I | 2969 | 46.1 | 655 | 42.4 |
| II | 3315 | 35.9 | 606 | 29.0 |
| III | 3392 | 33.0 | 623 | 25.0 |
| IV | 4010 | 35.1 | 756 | 30.0 |
| V | 2769 | 27.8 | 469 | 21.7 |
| VI | 2375 | 40.3 | 518 | 29.2 |
| VII | 2329 | 23.1 | 470 | 36.1 |

As will be seen from the above table, compositions in accordance with the invention exhibit high bioavailability (AUC and Cmax.) coupled with relatively low variability in subject response both for AUC and Cmax.

Comparable advantageous results may be obtained employing other compositions in accordance with examples 1,2,4,5 and 7 herein, in particular the compositions of example 1.

The advantageous properties of the compositions of the invention on oral administration may also be demonstrated in clinical trials, e.g. performed as follows:

Trial subjects are adult volunteers, e.g. professionally educated males of from 30 to 55 years. Trial groups suitably comprise 12 subjects.

The following inclusion/exclusion criteria are applied:
Inclusion: Normal screening ECG; normal blood-pressure and heart rate; body weight=50–95 kg.

Exclusion: Clinically significant intercurrent medical condition which might interfere with drug absorption, distribution, metabolism, excretion or safety; symptoms of a significant clinical illness in the two-week pre-trial period; clinically relevant abnormal laboratory values or electrocardiogram; need for concomitant medication during the entire course of the study; administration of any drug known to have a well-defined potential toxicity to a major organ system within the previous 3 months; administration of any investigational drug within 6 weeks prior to entry into the trial; history of drug or alcohol abuse; loss of 500 ml or more blood within the past 3 month period; adverse drug reaction or hypersensitivity; history of allergy requiring drug therapy; Hep.-B/HIV-positive.

Complete physical examination and ECG is performed pre- and post-trial. The following parameters are evaluated within 1-month periods pre- and post-trial:

Blood:—red blood cell count, haemoglobin, hematocrit, erythrocyte sedimentation, white blood cell count, smear, platelet count and fasting glucose;

Serum/plasma—total protein and electrophoresis, cholesterol, triglycerides, Na$^-$, K$^+$, Fe$^{++}$, Ca$^{-+}$, Cl$^-$ creatinine, urea, uric acid, SCOT, SGPT, -GT, alkaline phosphatase, total bilirubin, α-amylase; Urine—pH, microalbumin, glucose, erythrocytes, ketone bodies, sediment.

Creatinine clearance is also determined 1-month prior to trial entry.

Subjects each receive trial compositions in randomised sequence. Compositions are administered orally, once to a total dose of 150 mg cyclosporin, e.g. Ciclosporin, and at least 14 days are allowed between each administration.

Administration is performed in the morning after an overnight fast of 10 hrs. with only water allowed. Only caffein-free beverages are permitted within the 24 hr. period following administration. Subjects are not allowed to smoke within the 12 hr. period following administration. Subjects receive a standardised lunch 4 hrs. following administration.

Blood samples (2 ml) are taken 1 hr. prior to administration and post-administration at 0.25, 0.5, 1, 1.5, 2, 2.5, 3, 3.5, 4, 4.5, 5, 6, 9, 12, 14, 24, 28 and 32 hrs. For determination of creatinine 2 ml blood samples are taken immediately prior to administration and at 12, 24 and 48 hrs. post-administration. Samples for cyclosporin determination are collected in two EDTA coated polystyrene tubes (1 ml each) at each time point and are deep frozen at −20° C. after gentle agitation. Cyclosporin is assayed in whole blood using RIA with specific and/or non-specific MAB assay—detection limit in both cases=ca. 10 ng/ml.

In one such trial COMPOSTION I above in accordance with the invention (hard gelatin encapsulated form) is compared with COMPOSITION X.

| COMPOSITION X [COMPARATIVE (ART) COMPOSITION] Unit dosage form (soft gelatin capsule) comprising | |
|---|---|
| Ciclosporin | 50 mg |
| Labrafil | 150 mg |
| Ethanol | 50 mg |
| Maize oil | 213 mg |
| Total | 463 mg/dosage. |

(=current Sandimmun oral, drink solution)

In a trial performed in this manner a bioavailability level of 149.0% (±48) is recorded for COMPOSITION I as compared with COMPOSITION X (for which bioavailability achieved is set as 100%). AUC values (0–32 hrs. ng.h/ml) and Cmax. values (ng/ml) established for COMPOSITION I are 2992 (±627) and 882 (±18) respectively as compared with 2137 (±606) and 515 (±180) for COMPOSITION X.

Figs. III and IV attached provide superimposed graphical representations from such a trial of whole blood Ciclosporin concentrations recorded for all 12 trial participants following single oral administrations of COMPOSITION I (Fig. III) and COMPOSITION X (Fig. IV), each in an amount providing a Ciclosporin dosage of 150 mg, as determined by specific monoclonal RIA. Blood concentration (in ng/ml) is recorded vertically, and time (in hrs.) horizontally.

Comparison of Figs. III and IV clearly demonstrates the marked reduction in variability of inter-subject response with respect to bioavailability parameters recorded, on administration of COMPOSITION I as compared with COMPOSITION X. The determined coefficient of variation [(standard deviation/mean value)$_x$ 100] with respect to Cmax. for COMPOSITION X is 35% as compared with a value of only 20% for COMPOSITION I.

Similar or equivalent results may be obtained following oral administration of other compositions in accordance with the invention, e.g. as herein described in the examples, in particular the compositions of example 1.

In Vivo Testing For Topical Forms

Allergic Contact Dermatitis Test in the Guinea Pig

Guinea pigs (Hartley, male, 400–500 g) are sensitised by application of 50μl, 0.5% DNFB in acetone/olive oil (4:1) applied to marked areas on the shaven, left and right flank. This second challenge exposure induces an allergic inflammation, leading to reddening and cellular infiltration (thickening) of the skin. Test composition (e.g. in accordance with example 3,6.1 or 6.2 above) in an amount of from 200–250 mg is applied with a spatula to the DNFB treated area of the right flank. The left flank is similarly treated with placebo as control. Application of test composition/placebo is effected 5× at intrvals of 20 mins., 8 hrs., 24 hrs., 32 hrs., and 48 hrs., after the challenge. Skin thickness at the site of application is determined before each application, and again 8 hrs. after the last application, by raising the skin into a fold and measuring the thickness of this. Degree of reddening or inflammation is also estimated visually on a scale of from 0 to 4. Efficacy of test preparation in preventing inflammatory response is determined by comparison with results recorded for placebo treated flanks.

In the above test method substantial reduction in skin thickening as compared with placebo are achieved following first application of test composition, e.g. in accordance with examples 3,6.1 or 6.2, continuing throught treatment until completion of the experiment.

The following results are recorded for the composition of example 3

| TIME AFTER CHALLENGE (HRS) | 8 | 24 | 32 | 48 | 56 |
|---|---|---|---|---|---|
| % INHIBITION OF SKIN THICKNESS/ US PLACEBO CONTROL | 56 | 68 | 76 | 75 | 73 |

We claim:

1. A method of orally administering a pharmaceutical composition, said method comprising orally administering to a patient in need of cyclosporin A therapy a composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-in-water microemulsion having particles of less than 2,000 Å is spontaneously formed.

2. The method of claim 1 wherein the particles have a maximum size of less than 1,500 Å.

3. The method of claim 1 wherein the maximum size of the particles is from 100 to 1,000 Å.

4. The method of claim 1 wherein the dilution with water is to a ratio of 1 part by weight of composition to 1 part by weight of water.

5. The method of claim 1 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

6. The method of claim 1 comprising about 2 to about 45% by weight of lipophilic component, based on the total weight of the composition.

7. The method of claim 1 comprising about 20 to about 90% by weight of hydrophilic surfactant, based on the total weight of the composition.

8. The method of claim 1 comprising about 0.5 to about 90% by weight of hydrophilic component, about 2 to about 45% by weight of lipophilic component and about 20 to about 90% by weight of hydrophilic surfactant, all weights based on the total weight of the composition.

9. The method of claim 1 wherein said hydrophilic surfactant is a polyoxyethylene glycolated natural vegetable oil.

10. The method of claim 1 wherein said hydrophilic surfactant is a polyoxyethylene glycolated hydrogenated vegetable oil.

11. The method of claim 1 wherein said hydrophilic surfactant is a polyoxyethylene-sorbitan-fatty acid ester.

12. The method of claim 11 wherein said hydrophilic polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoxyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

13. The method of claim 1 wherein said hydrophilic surfactant is a polyoxyethylene fatty acid ester.

14. The method of claim 1 wherein said composition further comprises ethanol.

15. The method of claim 1 comprising about 5 to about 15% by weight of cyclosporin A, based on the total weight of the composition.

16. The method of claim 1 comprising a cyclosporin A to hydrophilic surfactant ratio of about 1:1 to about 1:10, based on parts per weight.

17. A method of orally administering a pharmaceutical composition, said method comprising orally administering to a patient in need of cyclosporin A therapy a composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-in-water microemulsion having an average particle size of less than about 1,500 Å is spontaneously formed.

18. The method of claim 17 wherein the average particle size is less than about 1,000 Å.

19. The method of claim 17 wherein the average particle size is from about 150 to less than about 1,000 Å.

20. The method of claim 17 wherein the dilution with water is to a ratio of 1 part by weight of composition to 1 part by weight of water.

21. The method of claim 17 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

22. The method of claim 17 comprising about 2 to about 45% by weight of lipophilic component, based on the total weight of the composition.

23. The method of claim 17 comprising about 20 to about 90% by weight of hydrophilic surfactant, based on the total weight of the composition.

24. The method of claim 17 comprising about 0.5 to about 90% by weight of hydrophilic component, about 2 to about 45% by weight of lipophilic component and about 20 to about 90% by weight of hydrophilic surfactant, all weights based on the total weight of the composition.

25. The method of claim 17 wherein said hydrophilic surfactant is a polyoxyethylene glycolated natural vegetable oil.

26. The method of claim 17 wherein said hydrophilic surfactant is a polyoxyethylene glycolated hydrogenated vegetable oil.

27. The method of claim 17 wherein said hydrophilic surfactant is a polyoxyethylene-sorbitan-fatty acid ester.

28. The method of claim 17 wherein said polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

29. The method of claim 17 wherein said hydrophilic surfactant is a polyoxyethylene fatty acid ester.

30. The method of claim 17 wherein said composition further comprises ethanol.

31. The method of claim 17 comprising about 5 to about 15% by weight of cyclosporin A, based on the total weight of the composition.

32. The method of claim 17 comprising a cyclosporin A to hydrophilic surfactant ratio of about 1:1 to about 1:10, based on parts per weight.

33. A method of reducing the variability of bioavailability levels of cyclosporin A for patients during cyclosporin A therapy, said method comprising orally administering a pharmaceutical composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-in-water microemulsion having particles of less than 2,000 Å is spontaneously formed.

34. The method of claim 33 wherein the particles have a maximum size of less than 1,500 Å.

35. The method of claim 33 wherein the maximum size of the particles is from 100 to 1,000 Å.

36. The method of claim 33 wherein the dilution with water is to a ratio of 1 part by weight of composition to 1 part by weight of water.

37. The method of claim 33 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

38. The method of claim 33 comprising about 2 to about 45% by weight of lipophilic component, based on the total weight of the composition.

39. The method of claim 33 comprising about 20 to about 90% by weight of hydrophilic surfactant, based on the total weight of the composition.

40. The method of claim 33 comprising about 0.5 to about 90% by weight of hydrophilic component, about 2 to about 45% by weight of lipophilic component and about 20 to about 90% by weight of hydrophilic surfactant, all weights based on the total weight of the composition.

41. The method of claim 33 wherein said hydrophilic surfactant is a polyoxyethylene glycolated natural vegetable oil.

42. The method of claim 33 wherein said hydrophilic surfactant is a polyoxyethylene glycolated hydrogenated vegetable oil.

43. The method of claim 33 wherein said hydrophilic surfactant is a polyoxyethylene-sorbitan-fatty acid ester.

44. The method of claim 33 wherein said hydrophilic polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoxyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

45. The method of claim 33 wherein said hydrophilic surfactant is a polyoxyethylene fatty acid ester.

46. The method of claim 33 wherein said composition further comprises ethanol.

47. The method of claim 33 comprising about 5 to about 15% by weight of cyclosporin A, based on the total weight of the composition.

48. The method of claim 33 comprising a cyclosporin A to hydrophilic surfactant ratio of about 1:1 to about 1:10, based on parts per weight.

49. A method of reducing the variability of bioavailability levels of cyclosporin A for patients during cyclosporin A therapy, said method comprising orally administering a pharmaceutical composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-in-water microemulsion having an average particle size of less than about 1,500 Å is spontaneously formed.

50. The method of claim 49 wherein the average particle size is less than about 1,000 Å.

51. The method of claim 49 wherein the average particle size is from about 150 to less than about 1,000 Å.

52. The method of claim 49 wherein the dilution with water is to a ratio of 1 part by weight of composition to 1 part by weight of water.

53. The method of claim 49 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

54. The method of claim 49 comprising about 2 to about 45% by weight of lipophilic component, based on the total weight of the composition.

55. The method of claim 49 comprising about 20 to about 90% by weight of hydrophilic surfactant, based on the total weight of the composition.

56. The method of claim 49 comprising about 0.5 to about 90% by weight of hydrophilic component, about 2 to about 45% by weight of lipophilic component and about 20 to about 90% by weight of hydrophilic surfactant, all weights based on the total weight of the composition.

57. The method of claim 49 wherein said hydrophilic surfactant is a polyoxyethylene glycolated natural vegetable oil.

58. The method of claim 49 wherein said hydrophilic surfactant is a polyoxyethylene glycolated hydrogenated vegetable oil.

59. The method of claim 49 wherein said hydrophilic surfactant is a polyoxyethylene-sorbitan-fatty acid ester.

60. The method of claim 59 wherein said hydrophilic polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoxyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

61. The method of claim 49 wherein said hydrophilic surfactant is a polyoxyethylene fatty acid ester.

62. The method of claim 49 wherein said composition further comprises ethanol.

63. The method of claim 49 comprising about 5 to about 15% by weight of cyclosporin A, based on the total weight of the composition.

64. The method of claim 49 comprising a cyclosporin A to hydrophilic surfactant ratio of about 1:1 to about 1:10, based on parts per weight.

65. An oral pharmaceutical composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-in-water microemulsion having particles of less than 2,000 Å is spontaneously formed.

66. The composition of claim 65 wherein the particles have a maximum size of less than 1,500 Å.

67. The composition of claim 65 wherein the maximum size of the particles is from 100 to 1,000 Å.

68. The composition of claim 65 wherein the dilution with water is to a ratio of 1 part by weight of composition to 1 part by weight of water.

69. The composition of claim 65 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

70. The composition of claim 65 comprising about 2 to about 45% by weight of lipophilic component, based on the total weight of the composition.

71. The composition of claim 65 comprising about 20 to about 90% by weight of hydrophilic surfactant, based on the total weight of the composition.

72. The composition of claim 65 comprising about 0.5 to about 90% by weight of hydrophilic component, about 2 to about 45% by weight of lipophilic component and about 20 to about 90% by weight of hydrophilic surfactant, all weights based on the total weight of the composition.

73. The composition of claim 65 wherein said hydrophilic surfactant is a polyoxyethylene glycolated natural vegetable oil.

74. The composition of claim 65 wherein said hydrophilic surfactant is a polyoxyethylene glycolated hydrogenated vegetable oil.

75. The composition of claim 65 wherein said hydrophilic surfactant is a polyoxyethylene-sorbitan-fatty acid ester.

76. The composition of claim 75 wherein said hydrophilic polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoxyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

77. The composition of claim 65 wherein said hydrophilic surfactant is a polyoxyethylene fatty acid ester.

78. The composition of claim 65 wherein said composition further comprises ethanol.

79. The composition of claim 65 comprising about 5 to about 15% by weight of cyclosporin A, based on the total weight of the composition.

80. The composition of claim 65 comprising a cyclosporin A to hydrophilic surfactant ratio of about 1:1 to about 1:10, based on parts per weight.

81. An oral pharmaceutical composition comprising about 5 to about 25% by weight of cyclosporin A, about 0.5 to about 90% by weight of a propylene glycol hydrophilic component, about 0.5 to about 90% by weight of a lipophilic component and about 0.5 to about 90% by weight of a hydrophilic surfactant, all weight percents being based on the total weight of the composition, the relative proportion of said cyclosporin A, hydrophilic component, lipophilic component and hydrophilic surfactant being such that upon dilution of said composition with adequate water, an oil-inwater microemulsion having an average particle size of less than about 1,500 Å is spontaneously formed.

82. The composition of claim 81 wherein the average particle size is less than about 1,000 Å.

83. The composition of claim 81 wherein the average particle size is from about 150 to less than about 1,000 Å.

84. The composition of claim 81 wherein the dilution with water is to a ratio of 1 part by weight of composition to 1 part by weight of water.

85. The composition of claim 81 wherein the hydrophilic surfactant is selected from the group consisting of polyoxyethylene glycolated natural vegetable oil, polyoxyethylene glycolated hydrogenated vegetable oil, polyoxyethylene-sorbitan-fatty acid ester and polyoxyethylene fatty acid ester.

86. The composition of claim 81 comprising about 2 to about 45% by weight of lipophilic component, based on the total weight of the composition.

87. The composition of claim 81 comprising about 20 to about 90% by weight of hydrophilic surfactant, based on the total weight of the composition.

88. The composition of claim 81 comprising about 0.5 to about 90% by weight of hydrophilic component, about 2 to about 45% by weight of lipophilic component and about 20 to about 90% by weight of hydrophilic surfactant, all weights based on the total weight of the composition.

89. The composition of claim 81 wherein said hydrophilic surfactant is a polyoxyethylene glycolated natural vegetable oil.

90. The composition of claim 81 wherein said hydrophilic surfactant is a polyoxyethylene glycolated hydrogenated vegetable oil.

91. The composition of claim 81 wherein said hydrophilic surfactant is a polyoxyethylene-sorbitan-fatty acid ester.

92. The composition of claim 91 wherein said hydrophilic polyoxyethylene-sorbitan-fatty acid ester is selected from the group consisting of polyoxyethylene(20)sorbitanmonolaurate, polyoxyethylene(20)sorbitanmonopalmitate, polyoxyethylene(20)sorbitanmonostearate, polyoxyethylene(20)sorbitanmonooleate, polyoxyethylene(20)sorbitantristearate, polyoxyethylene(20)sorbitantrioleate, polyoxyethylene(4)sorbitanmonolaurate, polyoxyethylene(4)sorbitanmonostearate and polyoxyethylene(5)sorbitanmonooleate.

93. The composition of claim 81 wherein said hydrophilic surfactant is a polyoxyethylene fatty acid ester.

94. The composition of claim 81 wherein said composition further comprises ethanol.

95. The composition of claim 81 comprising about 5 to about 15% by weight of cyclosporin A, based on the total weight of the composition.

96. The composition of claim 81 comprising a cyclosporin A to hydrophilic surfactant ratio of about 1:1 to about 1:10, based on parts per weight.

* * * * *